United States Patent
McClurken et al.

(10) Patent No.: US 8,475,455 B2
(45) Date of Patent: Jul. 2, 2013

(54) FLUID-ASSISTED ELECTROSURGICAL SCISSORS AND METHODS

(75) Inventors: Michael E. McClurken, Durham, NH (US); Roger D. Greeley, Portsmouth, NH (US); John W. Berry, Bel Air, MD (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1337 days.

(21) Appl. No.: 10/532,704

(22) PCT Filed: Oct. 28, 2003

(86) PCT No.: PCT/US03/34306
§ 371 (c)(1),
(2), (4) Date: May 2, 2006

(87) PCT Pub. No.: WO2004/039416
PCT Pub. Date: May 13, 2004

(65) Prior Publication Data
US 2006/0235379 A1 Oct. 19, 2006

Related U.S. Application Data

(60) Provisional application No. 60/422,190, filed on Oct. 29, 2002.

(51) Int. Cl.
*A61B 18/14* (2006.01)

(52) U.S. Cl.
USPC ............................... 606/52; 606/51; 606/207

(58) Field of Classification Search
USPC ...................... 606/32–52, 205–207
See application file for complete search history.

(56) References Cited

U.S. PATENT DOCUMENTS

| 623,022 | A | | 4/1899 | Johnson |
|---|---|---|---|---|
| 1,735,271 | A | | 11/1929 | Groff |
| 1,814,791 | A | | 7/1931 | Ende |
| 2,002,594 | A | | 5/1935 | Wappler et al. |
| 2,031,682 | A | | 2/1936 | Wappler et al. |
| 2,102,270 | A | | 12/1937 | Hyams |
| 2,275,167 | A | | 3/1942 | Bierman |
| 2,568,234 | A | * | 9/1951 | Haufrect .................. 606/174 |
| 2,888,928 | A | | 6/1959 | Seiger |
| 3,084,433 | A | * | 4/1963 | Kimmel .................. 30/254 |
| 3,163,166 | A | | 12/1964 | Brant et al. |
| 3,682,130 | A | | 8/1972 | Jeffers |

(Continued)

FOREIGN PATENT DOCUMENTS

| DE | 1 007 960 | 5/1957 |
|---|---|---|
| EP | 0 175 595 | 3/1986 |

(Continued)

OTHER PUBLICATIONS

Supplemental European Search Report dated Mar. 21, 2006 issued in related European Patent Application No. 03781437.3-2305.

*Primary Examiner* — Linda Dvorak
*Assistant Examiner* — Ronald Hupczey, Jr.
(74) *Attorney, Agent, or Firm* — Jeffrey J. Hohenshell

(57) ABSTRACT

An electrosurgical scissors comprising an end effector comprising a first blade member and a second blade member, the first blade member and the second blade member pivotally connected; an electrical connector configured to couple the scissors to a power source; and a fluid passage in fluid communication with at least one fluid outlet.

20 Claims, 12 Drawing Sheets

U.S. PATENT DOCUMENTS

| | | | |
|---|---|---|---|
| 3,750,650 | A | 8/1973 | Ruttgers |
| 3,901,241 | A | 8/1975 | Allen, Jr. |
| 4,037,590 | A | 7/1977 | Dohring et al. |
| 4,060,088 | A | 11/1977 | Morrison, Jr. et al. |
| 4,116,198 | A | 9/1978 | Roos |
| 4,244,371 | A | 1/1981 | Farin |
| 4,276,874 | A | 7/1981 | Wolvek et al. |
| 4,301,802 | A | 11/1981 | Poler |
| 4,307,720 | A | 12/1981 | Weber, Jr. |
| 4,321,931 | A | 3/1982 | Hon |
| 4,326,529 | A | 4/1982 | Doss et al. |
| 4,342,218 | A | 8/1982 | Fox |
| 4,355,642 | A | 10/1982 | Alferness |
| 4,381,007 | A | 4/1983 | Doss |
| 4,532,924 | A | 8/1985 | Auth et al. |
| 4,548,207 | A | 10/1985 | Reimels |
| 4,567,890 | A | 2/1986 | Ohta et al. |
| 4,602,628 | A | 7/1986 | Allen, Jr. |
| 4,671,274 | A | 6/1987 | Sorochenko |
| 4,674,499 | A | 6/1987 | Pao |
| 4,920,982 | A | 5/1990 | Goldstein |
| 4,931,047 | A | 6/1990 | Broadwin et al. |
| 4,932,952 | A | 6/1990 | Wojciechowicz, Jr. |
| 4,943,290 | A | 7/1990 | Rexroth et al. |
| 4,950,232 | A | 8/1990 | Ruzicka et al. |
| 4,976,711 | A | 12/1990 | Parins et al. |
| 4,985,030 | A | 1/1991 | Melzer et al. |
| 4,998,933 | A | 3/1991 | Eggers et al. |
| 5,009,656 | A | 4/1991 | Reimels |
| 5,013,312 | A | 5/1991 | Parins et al. |
| 5,035,696 | A | 7/1991 | Rydell |
| 5,071,419 | A | 12/1991 | Rydell et al. |
| 5,080,660 | A | 1/1992 | Buelna |
| 5,122,138 | A | 6/1992 | Manwaring |
| 5,125,928 | A | 6/1992 | Parins et al. |
| 5,147,357 | A | 9/1992 | Rose et al. |
| 5,151,102 | A | 9/1992 | Kamiyama et al. |
| 5,156,613 | A | 10/1992 | Sawyer |
| 5,167,659 | A | 12/1992 | Ohtomo et al. |
| 5,171,311 | A | 12/1992 | Rydell et al. |
| 5,190,541 | A | 3/1993 | Abele et al. |
| 5,195,959 | A | 3/1993 | Smith |
| 5,197,963 | A | 3/1993 | Parins |
| 5,197,964 | A | 3/1993 | Parins |
| 5,217,460 | A | 6/1993 | Knoepfler |
| 5,234,428 | A | 8/1993 | Kaufman |
| 5,242,441 | A | 9/1993 | Avitall |
| 5,242,442 | A | 9/1993 | Hirschfeld |
| 5,269,780 | A | 12/1993 | Roos |
| 5,269,781 | A | 12/1993 | Hewell, III |
| 5,277,696 | A | 1/1994 | Hagen |
| 5,281,215 | A | 1/1994 | Milder |
| 5,281,216 | A | 1/1994 | Klicek |
| 5,282,799 | A | 2/1994 | Rydell |
| 5,290,286 | A | 3/1994 | Parins |
| 5,300,087 | A * | 4/1994 | Knoepfler ............... 606/207 |
| 5,313,943 | A | 5/1994 | Houser et al. |
| 5,318,589 | A * | 6/1994 | Lichtman ............... 606/205 |
| 5,322,055 | A * | 6/1994 | Davison et al. ............ 601/2 |
| 5,322,503 | A | 6/1994 | Desai |
| 5,330,521 | A | 7/1994 | Cohen |
| 5,334,193 | A | 8/1994 | Nardella |
| 5,342,357 | A | 8/1994 | Nardella |
| 5,342,359 | A | 8/1994 | Rydell |
| 5,348,554 | A | 9/1994 | Imran et al. |
| 5,352,222 | A * | 10/1994 | Rydell ..................... 606/37 |
| 5,364,394 | A | 11/1994 | Mehl |
| 5,383,874 | A | 1/1995 | Jackson et al. |
| 5,383,876 | A | 1/1995 | Nardella |
| 5,395,312 | A | 3/1995 | Desai |
| 5,395,363 | A | 3/1995 | Billings et al. |
| 5,401,272 | A | 3/1995 | Perkins |
| 5,403,311 | A | 4/1995 | Abele et al. |
| 5,403,312 | A | 4/1995 | Yates et al. |
| 5,405,344 | A | 4/1995 | Williamson et al. |
| 5,405,376 | A | 4/1995 | Mulier et al. |
| 5,417,672 | A | 5/1995 | Nita et al. |
| 5,417,709 | A * | 5/1995 | Slater ..................... 606/205 |
| 5,431,649 | A | 7/1995 | Mulier et al. |
| 5,433,708 | A | 7/1995 | Nichols et al. |
| 5,437,662 | A | 8/1995 | Nardella |
| 5,437,664 | A | 8/1995 | Cohen et al. |
| 5,441,498 | A | 8/1995 | Perkins |
| 5,441,503 | A | 8/1995 | Considine et al. |
| 5,445,638 | A | 8/1995 | Rydell et al. |
| 5,456,682 | A | 10/1995 | Edwards et al. |
| 5,456,684 | A | 10/1995 | Schmidt et al. |
| 5,458,596 | A | 10/1995 | Lax et al. |
| 5,458,597 | A | 10/1995 | Edwards et al. |
| 5,458,598 | A | 10/1995 | Feinberg et al. |
| 5,460,629 | A | 10/1995 | Shlain et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,487,385 | A | 1/1996 | Avitall |
| 5,490,819 | A | 2/1996 | Nicholas et al. |
| 5,500,012 | A | 3/1996 | Brucker et al. |
| 5,514,130 | A | 5/1996 | Baker |
| 5,522,815 | A | 6/1996 | Durgin, Jr. et al. |
| 5,536,267 | A | 7/1996 | Edwards et al. |
| 5,540,562 | A | 7/1996 | Giter |
| 5,542,928 | A | 8/1996 | Evans et al. |
| 5,558,671 | A | 9/1996 | Yates |
| 5,562,503 | A | 10/1996 | Ellman et al. |
| 5,562,703 | A | 10/1996 | Desai |
| 5,564,440 | A | 10/1996 | Swartz et al. |
| 5,569,242 | A | 10/1996 | Lax et al. |
| 5,569,243 | A | 10/1996 | Kortenbach et al. |
| 5,573,424 | A | 11/1996 | Poppe |
| 5,573,533 | A | 11/1996 | Strul |
| 5,575,810 | A | 11/1996 | Swanson et al. |
| 5,584,872 | A | 12/1996 | LaFontaine et al. |
| 5,599,346 | A | 2/1997 | Edwards et al. |
| 5,599,350 | A | 2/1997 | Schulze et al. |
| 5,605,539 | A | 2/1997 | Buelna et al. |
| 5,609,151 | A | 3/1997 | Mulier et al. |
| 5,611,813 | A * | 3/1997 | Lichtman ................. 606/205 |
| 5,620,415 | A * | 4/1997 | Lucey et al. ............... 604/22 |
| 5,633,578 | A | 5/1997 | Eggers et al. |
| 5,637,110 | A * | 6/1997 | Pennybacker et al. .......... 606/46 |
| 5,640,955 | A | 6/1997 | Ockuly et al. |
| 5,643,197 | A | 7/1997 | Brucker et al. |
| 5,647,869 | A | 7/1997 | Goble et al. |
| 5,647,871 | A | 7/1997 | Levine et al. |
| 5,653,692 | A | 8/1997 | Masterson et al. |
| 5,658,281 | A * | 8/1997 | Heard ..................... 606/48 |
| 5,660,836 | A | 8/1997 | Knowlton |
| 5,676,662 | A | 10/1997 | Fleischhacker et al. |
| 5,676,693 | A | 10/1997 | LaFontaine |
| 5,681,282 | A | 10/1997 | Eggers et al. |
| 5,683,366 | A | 11/1997 | Eggers et al. |
| 5,683,384 | A | 11/1997 | Gough et al. |
| 5,687,723 | A | 11/1997 | Avitall |
| 5,688,270 | A | 11/1997 | Yates et al. |
| 5,693,045 | A | 12/1997 | Eggers |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,697,927 | A | 12/1997 | Imran et al. |
| 5,702,386 | A | 12/1997 | Stern et al. |
| 5,709,680 | A | 1/1998 | Yates et al. |
| 5,713,896 | A | 2/1998 | Nardella |
| 5,718,241 | A | 2/1998 | Ben-Haim et al. |
| 5,718,701 | A | 2/1998 | Shai et al. |
| 5,718,703 | A | 2/1998 | Chin |
| 5,722,400 | A | 3/1998 | Ockuly et al. |
| 5,725,524 | A | 3/1998 | Mulier et al. |
| 5,730,127 | A | 3/1998 | Avitall |
| 5,735,846 | A | 4/1998 | Panescu et al. |
| 5,743,903 | A | 4/1998 | Stern et al. |
| 5,746,739 | A | 5/1998 | Sutter |
| 5,749,869 | A | 5/1998 | Lindenmeier et al. |
| 5,755,717 | A | 5/1998 | Yates et al. |
| 5,755,753 | A | 5/1998 | Knowlton |
| 5,766,153 | A | 6/1998 | Eggers et al. |
| 5,766,167 | A | 6/1998 | Eggers et al. |

| Patent | Date | Inventor |
|---|---|---|
| 5,785,705 A | 7/1998 | Baker |
| 5,785,706 A | 7/1998 | Bednarek |
| 5,792,140 A | 8/1998 | Tu et al. |
| 5,797,905 A | 8/1998 | Fleischman et al. |
| 5,797,960 A | 8/1998 | Stevens et al. |
| 5,800,413 A | 9/1998 | Swartz et al. |
| 5,800,482 A | 9/1998 | Pomeranz |
| 5,807,393 A | 9/1998 | Williamson et al. |
| 5,807,395 A | 9/1998 | Mulier et al. |
| 5,810,764 A | 9/1998 | Eggers et al. |
| 5,810,805 A | 9/1998 | Sutcu et al. |
| 5,810,811 A | 9/1998 | Yates et al. |
| 5,817,093 A | 10/1998 | Williamson et al. |
| 5,823,956 A | 10/1998 | Roth et al. |
| 5,827,271 A | 10/1998 | Buysse et al. |
| 5,827,281 A * | 10/1998 | Levin ............................ 606/51 |
| 5,833,703 A | 11/1998 | Manushakian |
| 5,843,019 A | 12/1998 | Eggers et al. |
| 5,843,021 A | 12/1998 | Edwards et al. |
| 5,843,078 A | 12/1998 | Sharkey |
| 5,843,152 A | 12/1998 | Tu et al. |
| 5,855,614 A | 1/1999 | Stevens et al. |
| 5,860,951 A | 1/1999 | Eggers et al. |
| 5,860,974 A | 1/1999 | Abele |
| 5,861,002 A | 1/1999 | Desai |
| 5,861,021 A | 1/1999 | Thome et al. |
| 5,868,739 A | 2/1999 | Lindenmeier et al. |
| 5,871,469 A | 2/1999 | Eggers et al. |
| 5,871,524 A | 2/1999 | Knowlton |
| 5,873,855 A | 2/1999 | Eggers et al. |
| 5,876,398 A | 3/1999 | Mulier et al. |
| 5,888,198 A | 3/1999 | Eggers et al. |
| 5,891,095 A | 4/1999 | Eggers et al. |
| 5,891,141 A | 4/1999 | Rydell |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier et al. |
| 5,902,272 A | 5/1999 | Eggers et al. |
| 5,902,328 A | 5/1999 | LaFontaine et al. |
| 5,904,711 A | 5/1999 | Flom et al. |
| 5,906,613 A | 5/1999 | Mulier et al. |
| 5,913,854 A | 6/1999 | Maguire et al. |
| 5,913,856 A | 6/1999 | Chia et al. |
| 5,919,191 A | 7/1999 | Lennox et al. |
| 5,919,219 A | 7/1999 | Knowlton |
| 5,921,982 A | 7/1999 | Lesh et al. |
| 5,921,983 A | 7/1999 | Shannon, Jr. |
| 5,925,045 A | 7/1999 | Reimels et al. |
| 5,935,123 A | 8/1999 | Edwards et al. |
| 5,948,011 A | 9/1999 | Knowlton |
| 5,951,549 A | 9/1999 | Richardson et al. |
| 5,954,716 A | 9/1999 | Sharkey et al. |
| 5,957,919 A | 9/1999 | Laufer |
| 5,964,755 A | 10/1999 | Edwards |
| 5,971,983 A | 10/1999 | Lesh |
| 5,976,128 A | 11/1999 | Schilling et al. |
| 5,980,504 A | 11/1999 | Sharkey et al. |
| 5,980,516 A | 11/1999 | Mulier et al. |
| 5,989,248 A | 11/1999 | Tu et al. |
| 5,992,418 A | 11/1999 | de la Rama et al. |
| 5,993,412 A | 11/1999 | Deily et al. |
| 6,003,517 A | 12/1999 | Sheffield et al. |
| 6,004,316 A | 12/1999 | Laufer |
| 6,004,319 A | 12/1999 | Goble et al. |
| 6,007,570 A | 12/1999 | Sharkey et al. |
| 6,010,500 A | 1/2000 | Sherman et al. |
| 6,015,391 A | 1/2000 | Rishton et al. |
| 6,015,407 A | 1/2000 | Rieb et al. |
| 6,016,809 A | 1/2000 | Mulier et al. |
| 6,017,338 A | 1/2000 | Brucker et al. |
| 6,018,676 A | 1/2000 | Davis et al. |
| 6,019,757 A | 2/2000 | Scheldrup |
| 6,024,733 A | 2/2000 | Eggers et al. |
| 6,024,744 A * | 2/2000 | Kese et al. ............. 606/51 |
| 6,027,501 A | 2/2000 | Goble et al. |
| 6,030,379 A | 2/2000 | Panescu et al. |
| 6,032,077 A | 2/2000 | Pomeranz |
| 6,032,674 A | 3/2000 | Eggers et al. |
| 6,033,398 A | 3/2000 | Farley et al. |
| 6,035,238 A | 3/2000 | Ingle et al. |
| 6,036,687 A | 3/2000 | Laufer et al. |
| 6,045,532 A | 4/2000 | Eggers et al. |
| 6,047,700 A | 4/2000 | Eggers et al. |
| 6,048,333 A | 4/2000 | Lennox et al. |
| 6,053,172 A | 4/2000 | Hovda et al. |
| 6,053,912 A | 4/2000 | Panescu et al. |
| 6,056,744 A | 5/2000 | Edwards |
| 6,056,745 A | 5/2000 | Panescu et al. |
| 6,056,747 A | 5/2000 | Saadat et al. |
| 6,059,781 A | 5/2000 | Yamanashi et al. |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,068,627 A | 5/2000 | Orszulak et al. |
| 6,068,653 A | 5/2000 | LaFontaine |
| 6,071,280 A | 6/2000 | Edwards et al. |
| 6,073,051 A | 6/2000 | Sharkey et al. |
| 6,074,389 A | 6/2000 | Levine et al. |
| 6,080,151 A | 6/2000 | Swartz et al. |
| 6,081,749 A | 6/2000 | Ingle et al. |
| 6,083,237 A | 7/2000 | Huitema et al. |
| 6,086,585 A | 7/2000 | Hovda et al. |
| 6,086,586 A | 7/2000 | Hooven |
| 6,091,995 A | 7/2000 | Ingle et al. |
| 6,093,186 A | 7/2000 | Goble |
| 6,095,149 A | 8/2000 | Sharkey et al. |
| 6,096,037 A | 8/2000 | Mulier et al. |
| 6,099,514 A | 8/2000 | Sharkey et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,113,596 A * | 9/2000 | Hooven et al. ............... 606/42 |
| 6,113,597 A | 9/2000 | Eggers et al. |
| 6,117,109 A | 9/2000 | Eggers et al. |
| 6,122,549 A | 9/2000 | Sharkey et al. |
| H1904 H | 10/2000 | Yates et al. |
| 6,126,682 A | 10/2000 | Sharkey et al. |
| 6,135,999 A | 10/2000 | Fanton et al. |
| 6,141,576 A | 10/2000 | Littmann et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,165,169 A | 12/2000 | Panescu et al. |
| 6,165,175 A | 12/2000 | Wampler et al. |
| 6,168,594 B1 | 1/2001 | LaFontaine et al. |
| 6,171,275 B1 | 1/2001 | Webster, Jr. |
| 6,174,308 B1 | 1/2001 | Goble et al. |
| 6,174,309 B1 | 1/2001 | Wrublewski et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,190,384 B1 | 2/2001 | Ouchi |
| 6,193,715 B1 | 2/2001 | Wrublewski et al. |
| 6,193,716 B1 | 2/2001 | Shannon, Jr. |
| 6,203,542 B1 | 3/2001 | Ellsberry et al. |
| 6,210,402 B1 | 4/2001 | Olsen et al. |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,576 B1 | 4/2001 | Tu et al. |
| 6,221,039 B1 | 4/2001 | Durgin et al. |
| 6,221,069 B1 | 4/2001 | Daikuzono |
| 6,224,592 B1 | 5/2001 | Eggers et al. |
| 6,224,593 B1 | 5/2001 | Ryan et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,387 B1 | 5/2001 | Miller, III |

| Patent | Type | Date | Inventor |
|---|---|---|---|
| 6,238,391 | B1 | 5/2001 | Olsen et al. |
| 6,238,393 | B1 | 5/2001 | Mulier et al. |
| 6,241,753 | B1 | 6/2001 | Knowlton |
| 6,241,754 | B1 | 6/2001 | Swanson et al. |
| 6,251,110 | B1 | 6/2001 | Wampler |
| 6,254,600 | B1 | 7/2001 | Willink et al. |
| 6,258,086 | B1 | 7/2001 | Ashley et al. |
| 6,258,087 | B1 | 7/2001 | Edwards et al. |
| 6,261,311 | B1 | 7/2001 | Sharkey et al. |
| 6,264,650 | B1 | 7/2001 | Hovda et al. |
| 6,264,651 | B1 | 7/2001 | Underwood et al. |
| 6,264,652 | B1 | 7/2001 | Eggers et al. |
| 6,264,654 | B1 | 7/2001 | Swartz et al. |
| 6,266,551 | B1 | 7/2001 | Osadchy et al. |
| 6,277,112 | B1 | 8/2001 | Underwood et al. |
| 6,280,440 | B1 | 8/2001 | Gocho |
| 6,283,961 | B1 | 9/2001 | Underwood et al. |
| 6,283,988 | B1 | 9/2001 | Laufer et al. |
| 6,283,989 | B1 | 9/2001 | Laufer et al. |
| 6,290,715 | B1 | 9/2001 | Sharkey et al. |
| 6,293,942 | B1 | 9/2001 | Goble et al. |
| 6,293,945 | B1 | 9/2001 | Parins et al. |
| 6,296,636 | B1 | 10/2001 | Cheng et al. |
| 6,296,638 | B1 | 10/2001 | Davison et al. |
| 6,296,640 | B1 | 10/2001 | Wampler et al. |
| 6,299,633 | B1 | 10/2001 | Laufer |
| 6,302,903 | B1 | 10/2001 | Mulier et al. |
| 6,306,134 | B1 | 10/2001 | Goble et al. |
| 6,309,387 | B1 | 10/2001 | Eggers et al. |
| 6,311,090 | B1 | 10/2001 | Knowlton |
| 6,312,408 | B1 | 11/2001 | Eggers et al. |
| 6,312,430 | B1 | 11/2001 | Wilson et al. |
| 6,315,777 | B1 | 11/2001 | Comben |
| 6,322,549 | B1 | 11/2001 | Eggers et al. |
| 6,322,559 | B1 | 11/2001 | Daulton et al. |
| 6,327,505 | B1 | 12/2001 | Medhkour et al. |
| 6,328,735 | B1 | 12/2001 | Curley et al. |
| 6,328,736 | B1 | 12/2001 | Mulier et al. |
| 6,336,926 | B1 | 1/2002 | Goble |
| 6,350,262 | B1 | 2/2002 | Ashley |
| 6,350,276 | B1 | 2/2002 | Knowlton |
| 6,352,533 | B1 | 3/2002 | Ellman et al. |
| 6,355,032 | B1 | 3/2002 | Hovda et al. |
| 6,358,245 | B1 | 3/2002 | Edwards et al. |
| 6,358,248 | B1 | 3/2002 | Mulier et al. |
| 6,363,937 | B1 | 4/2002 | Hovda et al. |
| 6,371,956 | B1 | 4/2002 | Wilson et al. |
| 6,379,350 | B1 | 4/2002 | Sharkey et al. |
| 6,379,351 | B1 | 4/2002 | Thapliyal et al. |
| 6,391,025 | B1 | 5/2002 | Weinstein et al. |
| 6,391,028 | B1 | 5/2002 | Fanton et al. |
| 6,402,742 | B1 | 6/2002 | Blewett et al. |
| 6,409,722 | B1 | 6/2002 | Hoey et al. |
| 6,409,723 | B1 | 6/2002 | Edwards |
| H2037 | H | 7/2002 | Yates et al. |
| 6,416,507 | B1 | 7/2002 | Eggers et al. |
| 6,416,508 | B1 | 7/2002 | Eggers et al. |
| 6,416,509 | B1 | 7/2002 | Goble et al. |
| 6,425,877 | B1 | 7/2002 | Edwards |
| 6,432,103 | B1 | 8/2002 | Ellsberry et al. |
| 6,440,130 | B1 | 8/2002 | Mulier et al. |
| 6,443,952 | B1 | 9/2002 | Mulier et al. |
| 6,451,017 | B1 | 9/2002 | Moutafis et al. |
| 6,458,123 | B1 | 10/2002 | Brucker et al. |
| 6,458,130 | B1 | 10/2002 | Frazier et al. |
| 6,461,350 | B1 | 10/2002 | Underwood et al. |
| 6,461,354 | B1 | 10/2002 | Olsen et al. |
| 6,461,357 | B1 | 10/2002 | Sharkey et al. |
| 6,464,695 | B2 | 10/2002 | Hovda et al. |
| 6,468,270 | B1 | 10/2002 | Hovda et al. |
| 6,468,274 | B1 | 10/2002 | Alleyne et al. |
| 6,468,275 | B1 | 10/2002 | Wampler et al. |
| 6,471,698 | B1 | 10/2002 | Edwards et al. |
| 6,475,216 | B2 | 11/2002 | Mulier et al. |
| 6,478,793 | B1 | 11/2002 | Cosman et al. |
| 6,482,202 | B1 | 11/2002 | Goble et al. |
| 6,485,490 | B2 | 11/2002 | Wampler et al. |
| 6,488,680 | B1 | 12/2002 | Francischelli et al. |
| 6,493,589 | B1 | 12/2002 | Medhkour et al. |
| 6,494,902 | B2 | 12/2002 | Hoey et al. |
| 6,497,704 | B2 | 12/2002 | Ein-Gal |
| 6,497,705 | B2 | 12/2002 | Comben |
| 6,506,189 | B1 | 1/2003 | Rittman, III et al. |
| 6,508,815 | B1 | 1/2003 | Strul et al. |
| 6,517,536 | B2 | 2/2003 | Hooven et al. |
| 6,526,320 | B2 | 2/2003 | Mitchell |
| 6,537,248 | B2 | 3/2003 | Mulier et al. |
| 6,537,272 | B2 | 3/2003 | Christopherson et al. |
| 6,539,265 | B2 | 3/2003 | Medhkour et al. |
| 6,558,379 | B1 | 5/2003 | Batchelor et al. |
| 6,558,385 | B1 | 5/2003 | McClurken et al. |
| 6,575,969 | B1 | 6/2003 | Rittman, III et al. |
| 6,577,902 | B1 | 6/2003 | Laufer et al. |
| 6,579,288 | B1 | 6/2003 | Swanson et al. |
| 6,585,732 | B2 | 7/2003 | Mulier et al. |
| 6,602,248 | B1 | 8/2003 | Sharps et al. |
| 6,603,988 | B2 | 8/2003 | Dowlatshahi |
| 6,610,060 | B2 | 8/2003 | Mulier et al. |
| 6,613,048 | B2 | 9/2003 | Mulier et al. |
| 6,623,515 | B2 | 9/2003 | Mulier et al. |
| 6,626,899 | B2 | 9/2003 | Houser et al. |
| 6,645,202 | B1 | 11/2003 | Pless et al. |
| 6,666,862 | B2 | 12/2003 | Jain et al. |
| 6,669,692 | B1 | 12/2003 | Nelson et al. |
| 6,676,660 | B2 | 1/2004 | Wampler |
| 6,679,882 | B1 | 1/2004 | Kornerup |
| 6,682,501 | B1 | 1/2004 | Nelson et al. |
| 6,682,527 | B2 | 1/2004 | Strul |
| 6,682,528 | B2 | 1/2004 | Frazier et al. |
| 6,685,700 | B2 | 2/2004 | Behl et al. |
| 6,685,701 | B2 | 2/2004 | Orszulak et al. |
| 6,685,704 | B2 | 2/2004 | Greep |
| 6,689,129 | B2 | 2/2004 | Baker |
| 6,689,131 | B2 | 2/2004 | McClurken |
| 6,692,489 | B1 | 2/2004 | Heim et al. |
| 6,694,984 | B2 | 2/2004 | Habib |
| 6,695,837 | B2 | 2/2004 | Howell |
| 6,695,840 | B2 | 2/2004 | Schulze |
| 6,699,240 | B2 | 3/2004 | Francischelli |
| 6,699,242 | B2 | 3/2004 | Heggeness |
| 6,699,244 | B2 | 3/2004 | Carranza et al. |
| 6,699,268 | B2 | 3/2004 | Kordis et al. |
| 6,702,810 | B2 | 3/2004 | McClurken et al. |
| 6,702,812 | B2 | 3/2004 | Cosmescu |
| 6,706,039 | B2 | 3/2004 | Mulier et al. |
| 6,712,074 | B2 | 3/2004 | Edwards et al. |
| 6,712,811 | B2 | 3/2004 | Underwood et al. |
| 6,712,813 | B2 | 3/2004 | Ellman et al. |
| 6,712,816 | B2 | 3/2004 | Hung et al. |
| 6,716,211 | B2 | 4/2004 | Mulier et al. |
| 6,719,754 | B2 | 4/2004 | Underwood et al. |
| 6,723,094 | B1 | 4/2004 | Desinger |
| 6,726,683 | B1 | 4/2004 | Shaw |
| 6,726,684 | B1 | 4/2004 | Woloszko et al. |
| 6,726,686 | B2 | 4/2004 | Buysse et al. |
| 6,730,081 | B1 | 5/2004 | Desai |
| 6,733,496 | B2 | 5/2004 | Ashley et al. |
| 6,733,498 | B2 | 5/2004 | Paton et al. |
| 6,733,501 | B2 | 5/2004 | Levine |
| 6,736,810 | B2 | 5/2004 | Hoey et al. |
| 6,740,058 | B2 | 5/2004 | Lal et al. |
| 6,740,079 | B1 | 5/2004 | Eggers et al. |
| 6,740,082 | B2 | 5/2004 | Shadduck |
| 6,740,084 | B2 | 5/2004 | Ryan |
| 6,740,102 | B2 | 5/2004 | Hess et al. |
| 6,743,197 | B1 | 6/2004 | Edwards |
| 6,743,229 | B2 | 6/2004 | Buysse et al. |
| 6,743,230 | B2 | 6/2004 | Lutze et al. |
| 6,746,447 | B2 | 6/2004 | Davison et al. |
| 6,755,825 | B2 | 6/2004 | Shoenman et al. |
| 6,755,827 | B2 | 6/2004 | Mulier et al. |
| 6,757,565 | B2 | 6/2004 | Sharkey et al. |
| 6,758,846 | B2 | 7/2004 | Goble et al. |
| 6,761,718 | B2 | 7/2004 | Madsen |
| 6,764,487 | B2 | 7/2004 | Mulier et al. |
| 6,770,070 | B1 | 8/2004 | Balbierz |
| 6,770,071 | B2 | 8/2004 | Woloszko et al. |
| 6,770,072 | B1 | 8/2004 | Truckai et al. |

| Patent No. | Date | Inventor(s) |
|---|---|---|
| 6,772,012 B2 | 8/2004 | Ricart et al. |
| 6,772,013 B1 | 8/2004 | Ingle et al. |
| 6,775,575 B2 | 8/2004 | Bommannan et al. |
| 6,776,780 B2 | 8/2004 | Mulier et al. |
| 6,780,177 B2 | 8/2004 | Shafirstein et al. |
| 6,780,180 B1 | 8/2004 | Goble et al. |
| 6,786,906 B1 | 9/2004 | Cobb |
| 6,796,981 B2 | 9/2004 | Wham et al. |
| 6,800,077 B1 | 10/2004 | Mucko et al. |
| 6,802,842 B2 | 10/2004 | Ellman et al. |
| 6,802,843 B2 | 10/2004 | Truckai et al. |
| 6,808,525 B2 | 10/2004 | Latterell et al. |
| 6,813,520 B2 | 11/2004 | Truckai et al. |
| 6,814,714 B1 | 11/2004 | Novak et al. |
| 6,814,731 B2 | 11/2004 | Swanson |
| 6,821,273 B2 | 11/2004 | Mollenauer |
| 6,827,713 B2 | 12/2004 | Bek et al. |
| 6,827,725 B2 | 12/2004 | Batchelor et al. |
| 6,832,997 B2 | 12/2004 | Uchida et al. |
| 6,835,195 B2 | 12/2004 | Schulze et al. |
| 6,836,688 B2 | 12/2004 | Ingle et al. |
| 6,843,789 B2 | 1/2005 | Goble |
| 6,845,264 B1 | 1/2005 | Skladnev et al. |
| 6,849,073 B2 | 2/2005 | Hoey et al. |
| 6,855,145 B2 | 2/2005 | Ciarrocca |
| 6,858,028 B2 | 2/2005 | Mulier et al. |
| 6,860,882 B2 | 3/2005 | Battles et al. |
| 6,863,669 B2 | 3/2005 | Spitzer |
| 6,864,686 B2 | 3/2005 | Novak et al. |
| 6,881,214 B2 | 4/2005 | Cosman et al. |
| 6,882,885 B2 | 4/2005 | Levy, Jr. et al. |
| 6,887,237 B2 | 5/2005 | McGaffigan |
| 6,887,240 B1 | 5/2005 | Lands et al. |
| 6,893,435 B2 | 5/2005 | Goble |
| 6,893,440 B2 | 5/2005 | Durgin et al. |
| 6,896,672 B1 | 5/2005 | Eggers et al. |
| 6,896,674 B1 | 5/2005 | Woloszko et al. |
| 6,899,712 B2 | 5/2005 | Moutafis et al. |
| 6,905,497 B2 | 6/2005 | Truckai et al. |
| 6,905,499 B1 | 6/2005 | Mucko et al. |
| 6,911,019 B2 | 6/2005 | Mulier et al. |
| 6,915,806 B2 | 7/2005 | Pacek et al. |
| 6,921,398 B2 | 7/2005 | Carmel et al. |
| 6,921,399 B2 | 7/2005 | Carmel et al. |
| 6,923,803 B2 | 8/2005 | Goble |
| 6,923,805 B1 | 8/2005 | LaFontaine et al. |
| 6,926,706 B1 | 8/2005 | Sealfon |
| 6,926,716 B2 | 8/2005 | Baker et al. |
| 6,926,717 B1 | 8/2005 | Garito et al. |
| 6,929,640 B1 | 8/2005 | Underwood et al. |
| 6,929,641 B2 | 8/2005 | Goble et al. |
| 6,929,642 B2 | 8/2005 | Xiao et al. |
| 6,929,644 B2 | 8/2005 | Truckai et al. |
| 6,929,645 B2 | 8/2005 | Battles et al. |
| 6,932,810 B2 | 8/2005 | Ryan |
| 6,932,815 B2 | 8/2005 | Sutter |
| 6,942,661 B2 | 9/2005 | Swanson |
| 6,949,096 B2 | 9/2005 | Davison et al. |
| 6,949,098 B2 | 9/2005 | Mulier et al. |
| 6,951,559 B1 | 10/2005 | Greep |
| 6,953,461 B2 | 10/2005 | McClurken et al. |
| 6,960,204 B2 | 11/2005 | Eggers et al. |
| 6,960,207 B2 | 11/2005 | Vanney et al. |
| 6,960,210 B2 | 11/2005 | Lands et al. |
| 6,962,589 B2 | 11/2005 | Mulier et al. |
| 6,964,274 B1 | 11/2005 | Ryan et al. |
| 6,964,661 B2 | 11/2005 | Rioux et al. |
| 6,966,907 B2 | 11/2005 | Goble |
| 6,966,909 B2 | 11/2005 | Marshall et al. |
| 6,971,394 B2 | 12/2005 | Sliwa, Jr. et al. |
| 6,974,452 B1 | 12/2005 | Gille et al. |
| 6,974,453 B2 | 12/2005 | Woloszko et al. |
| 6,979,332 B2 | 12/2005 | Adams |
| 6,984,231 B2 | 1/2006 | Goble et al. |
| 6,986,769 B2 | 1/2006 | Nelson et al. |
| 6,991,631 B2 | 1/2006 | Woloszko et al. |
| 7,001,380 B2 | 2/2006 | Goble |
| 7,001,382 B2 | 2/2006 | Gallo, Sr. |
| 7,004,941 B2 | 2/2006 | Tvinnereim et al. |
| 7,004,942 B2 | 2/2006 | Laird et al. |
| 7,008,419 B2 | 3/2006 | Shadduck |
| 7,008,421 B2 | 3/2006 | Daniel et al. |
| 7,033,348 B2 | 4/2006 | Alfano et al. |
| 7,033,356 B2 | 4/2006 | Latterell et al. |
| 7,041,096 B2 | 5/2006 | Malis et al. |
| 7,041,101 B2 | 5/2006 | Eggers |
| 7,041,102 B2 | 5/2006 | Truckai et al. |
| 7,052,494 B2 | 5/2006 | Goble et al. |
| 7,060,064 B2 | 6/2006 | Allen et al. |
| 7,063,670 B2 | 6/2006 | Sampson et al. |
| 7,066,932 B1 | 6/2006 | Morgan et al. |
| 7,066,936 B2 | 6/2006 | Ryan |
| 7,070,596 B1 | 7/2006 | Woloszko et al. |
| 7,070,604 B1 | 7/2006 | Garito et al. |
| 7,074,217 B2 | 7/2006 | Strul et al. |
| 7,074,219 B2 | 7/2006 | Levine et al. |
| 7,083,601 B1 | 8/2006 | Cosmescu |
| 7,087,051 B2 | 8/2006 | Bourne et al. |
| 7,087,053 B2 | 8/2006 | Vanney |
| 7,094,215 B2 | 8/2006 | Davison et al. |
| 7,101,387 B2 | 9/2006 | Garabedian et al. |
| 7,104,986 B2 | 9/2006 | Hovda et al. |
| 7,112,199 B2 | 9/2006 | Cosmescu |
| 7,115,139 B2 | 10/2006 | McClurken et al. |
| 7,125,406 B2 | 10/2006 | Given |
| 7,147,634 B2 | 12/2006 | Nesbitt |
| 7,147,635 B2 | 12/2006 | Ciarrocca |
| 7,147,637 B2 | 12/2006 | Goble |
| 7,147,638 B2 | 12/2006 | Chapman et al. |
| 7,150,746 B2 | 12/2006 | DeCesare et al. |
| 7,150,747 B1 | 12/2006 | McDonald et al. |
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |

| Pub. No. | Date | Inventor |
|---|---|---|
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |
| 2002/0156511 A1 | 10/2002 | Habib |
| 2002/0161364 A1* | 10/2002 | Mulier et al. ............ 606/49 |
| 2002/0169446 A1 | 11/2002 | Mulier et al. |
| 2002/0177846 A1 | 11/2002 | Mulier et al. |
| 2002/0183733 A1 | 12/2002 | Mulier et al. |
| 2002/0188284 A1 | 12/2002 | To et al. |
| 2002/0193851 A1 | 12/2002 | Silverman et al. |
| 2002/0198524 A1 | 12/2002 | Mulier et al. |
| 2003/0004510 A1 | 1/2003 | Wham et al. |
| 2003/0032955 A1 | 2/2003 | Mulier et al. |
| 2003/0073989 A1 | 4/2003 | Hoey et al. |
| 2003/0114850 A1 | 6/2003 | McClurken et al. |
| 2003/0181902 A1 | 9/2003 | Mulier et al. |
| 2003/0204185 A1 | 10/2003 | Sherman et al. |
| 2003/0216733 A1 | 11/2003 | McClurken et al. |
| 2004/0015162 A1 | 1/2004 | McGaffigan |
| 2004/0015163 A1 | 1/2004 | Buysse et al. |
| 2004/0015215 A1 | 1/2004 | Fredricks et al. |
| 2004/0015216 A1 | 1/2004 | DeSisto |
| 2004/0015218 A1 | 1/2004 | Finch et al. |
| 2004/0019350 A1 | 1/2004 | O'Brien et al. |
| 2004/0024395 A1 | 2/2004 | Ellman et al. |
| 2004/0024396 A1 | 2/2004 | Eggers |
| 2004/0024398 A1 | 2/2004 | Hovda et al. |
| 2004/0024399 A1 | 2/2004 | Sharps et al. |
| 2004/0030327 A1 | 2/2004 | Golan |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030333 A1 | 2/2004 | Goble |
| 2004/0034340 A1 | 2/2004 | Biscup |
| 2004/0034346 A1 | 2/2004 | Stern et al. |
| 2004/0034349 A1 | 2/2004 | Kirwan, Jr. et al. |
| 2004/0034400 A1 | 2/2004 | Ingle et al. |
| 2004/0039429 A1 | 2/2004 | Daniel et al. |
| 2004/0044341 A1 | 3/2004 | Truckai et al. |
| 2004/0054363 A1 | 3/2004 | Vaska et al. |
| 2004/0054365 A1 | 3/2004 | Goble |
| 2004/0054366 A1 | 3/2004 | Davison et al. |
| 2004/0054369 A1 | 3/2004 | Nelson et al. |
| 2004/0054370 A1 | 3/2004 | Given |
| 2004/0059328 A1 | 3/2004 | Daniel et al. |
| 2004/0059363 A1 | 3/2004 | Alvarez et al. |
| 2004/0064023 A1 | 4/2004 | Ryan et al. |
| 2004/0064137 A1 | 4/2004 | Pellegrino et al. |
| 2004/0068306 A1 | 4/2004 | Shadduck |
| 2004/0068307 A1 | 4/2004 | Goble |
| 2004/0073205 A1 | 4/2004 | Treat et al. |
| 2004/0073208 A1 | 4/2004 | Sutter |
| 2004/0078034 A1 | 4/2004 | Acker et al. |
| 2004/0078037 A1 | 4/2004 | Batchelor et al. |
| 2004/0078038 A1 | 4/2004 | Desinger et al. |
| 2004/0082946 A1 | 4/2004 | Malis et al. |
| 2004/0082952 A1 | 4/2004 | Dycus et al. |
| 2004/0087937 A1 | 5/2004 | Eggers et al. |
| 2004/0087939 A1 | 5/2004 | Eggers et al. |
| 2004/0087940 A1 | 5/2004 | Jahns et al. |
| 2004/0087943 A1 | 5/2004 | Dycus et al. |
| 2004/0088029 A1 | 5/2004 | Yamamoto |
| 2004/0092925 A1 | 5/2004 | Rizoiu et al. |
| 2004/0092926 A1 | 5/2004 | Hoey et al. |
| 2004/0097919 A1 | 5/2004 | Wellman et al. |
| 2004/0102770 A1 | 5/2004 | Goble |
| 2004/0102824 A1 | 5/2004 | Sharkey et al. |
| 2004/0116923 A1 | 6/2004 | Desinger |
| 2004/0122420 A1 | 6/2004 | Amoah |
| 2004/0122423 A1 | 6/2004 | Dycus et al. |
| 2004/0122494 A1 | 6/2004 | Eggers et al. |
| 2004/0138654 A1 | 7/2004 | Goble |
| 2004/0138655 A1 | 7/2004 | McClurken et al. |
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |
| 2004/0186535 A1 | 9/2004 | Knowlton |
| 2004/0193148 A1 | 9/2004 | Wham et al. |
| 2004/0193150 A1 | 9/2004 | Sharkey et al. |
| 2004/0193152 A1 | 9/2004 | Sutton et al. |
| 2004/0193211 A1 | 9/2004 | Voegele et al. |
| 2004/0199156 A1 | 10/2004 | Rioux et al. |
| 2004/0199160 A1 | 10/2004 | Slater |
| 2004/0206365 A1 | 10/2004 | Knowlton |
| 2004/0210213 A1 | 10/2004 | Fuimaono et al. |
| 2004/0210214 A1 | 10/2004 | Knowlton |
| 2004/0215181 A1 | 10/2004 | Christopherson et al. |
| 2004/0215182 A1 | 10/2004 | Lee |
| 2004/0215183 A1 | 10/2004 | Hoey et al. |
| 2004/0215184 A1 | 10/2004 | Eggers et al. |
| 2004/0215185 A1 | 10/2004 | Truckai et al. |
| 2004/0215188 A1 | 10/2004 | Mulier et al. |
| 2004/0215235 A1 | 10/2004 | Jackson et al. |
| 2004/0215296 A1 | 10/2004 | Ganz et al. |
| 2004/0220561 A1 | 11/2004 | Kirwan, Jr. et al. |
| 2004/0220562 A1 | 11/2004 | Garabedian et al. |
| 2004/0225288 A1 | 11/2004 | Buysse et al. |
| 2004/0230190 A1 | 11/2004 | Dahla et al. |
| 2004/0236322 A1 | 11/2004 | Mulier et al. |
| 2004/0236324 A1 | 11/2004 | Muller et al. |
| 2004/0243125 A1 | 12/2004 | Dycus et al. |
| 2004/0243163 A1 | 12/2004 | Casiano et al. |
| 2004/0249371 A1 | 12/2004 | Dycus et al. |
| 2004/0249374 A1 | 12/2004 | Tetzlaff et al. |
| 2004/0249425 A1 | 12/2004 | Roy et al. |
| 2004/0260279 A1 | 12/2004 | Goble et al. |
| 2004/0260280 A1 | 12/2004 | Sartor |
| 2004/0260368 A1 | 12/2004 | Ingle et al. |
| 2005/0010205 A1 | 1/2005 | Hovda et al. |
| 2005/0010212 A1 | 1/2005 | McClurken et al. |
| 2005/0015085 A1 | 1/2005 | McClurken et al. |
| 2005/0015086 A1 | 1/2005 | Platt |
| 2005/0015130 A1 | 1/2005 | Gill |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0033292 A1 | 2/2005 | Teitelbaum et al. |
| 2005/0038471 A1 | 2/2005 | Chan et al. |
| 2005/0043728 A1 | 2/2005 | Ciarrocca |
| 2005/0049583 A1 | 3/2005 | Swanson |
| 2005/0049586 A1 | 3/2005 | Daniel et al. |
| 2005/0055019 A1 | 3/2005 | Skarda |
| 2005/0055020 A1 | 3/2005 | Skarda |
| 2005/0059966 A1 | 3/2005 | McClurken et al. |
| 2005/0070888 A1 | 3/2005 | Dimatteo et al. |
| 2005/0070891 A1 | 3/2005 | DeSisto |
| 2005/0070894 A1 | 3/2005 | McClurken |
| 2005/0070896 A1 | 3/2005 | Daniel et al. |
| 2005/0080410 A1 | 4/2005 | Rioux et al. |
| 2005/0080413 A1 | 4/2005 | Canady |
| 2005/0085804 A1 | 4/2005 | McGaffigan |
| 2005/0085809 A1 | 4/2005 | Mucko et al. |
| 2005/0085880 A1 | 4/2005 | Truckai et al. |
| 2005/0090816 A1 | 4/2005 | McClurken et al. |

| Publication No. | Date | Name |
|---|---|---|
| 2005/0090819 A1 | 4/2005 | Goble |
| 2005/0096649 A1 | 5/2005 | Adams |
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | Weitkamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0071270 A1 | 3/2008 | Desinger et al. |

FOREIGN PATENT DOCUMENTS

| | | |
|---|---|---|
| EP | 0 853 922 | 7/1998 |
| EP | 1 095 627 A1 | 5/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 97/05829 A1 | 2/1997 |
| WO | WO 98/38932 A1 | 9/1998 |
| WO | WO 99/66850 A1 | 12/1999 |
| WO | WO 00/78240 A1 | 12/2000 |
| WO | WO 01/28444 A1 | 4/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

* cited by examiner

FLUID-ASSISTED ELECTROSURGICAL SCISSORS AND METHODS

CROSS REFERENCE TO RELATED APPLICATIONS

This patent application is a U.S. national stage application of PCT international patent application serial no. PCT/US2003/034306, filed Oct. 28, 2003, which claims priority under 35 U.S.C. §119(e) to U.S. provisional application Ser. No. 60/422,190, filed Oct. 29, 2002.

The entire disclosure of each of these patent applications is incorporated herein by reference to the extent it is consistent.

This application is being filed on 28 Oct. 2003 as a PCT International Patent application in the name of TissueLink Medical, Inc. (a U.S. national corporation), applicant for the designation of all countries except the US, and Michael E. McClurken, Roger D. Greeley, and John W. Berry (all US citizens), applicants for the designation of the US only.

FIELD

This invention relates generally to the field of medical devices, systems and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

As is well known in electrosurgery, with a monopolar device configuration, electrical power is delivered from a power source to an active terminal provided with the device. The electrical energy from the device then is passed through the patient generally to a large surface, electrically dispersive ground pad, often referred to as the return terminal, located on the back or other suitable anatomical location of the patient, and then back to the power source. Conversely, bipolar devices include both the active and return electrodes on the device. Electrical current flows from the active electrode generally through localized tissue and then to the return electrode and back to the power source.

One often cited advantage of bipolar devices as compared to monopolar devices is the elimination of electrical current flowing through the patient to a ground pad. However, devices such as bipolar scissors tend to be fairly complex in attempting to electrically isolate the active electrical terminal (pole) from the other return electrical terminal (pole). Furthermore, as disclosed in U.S. Pat. No. 5,658,281 in the name of Heard entitled "Bipolar Electrosurgical Scissors and Method Of Manufacture", one of the advantages of monopolar electrosurgical tools is that the surgeon can apply electrosurgical current whenever the conductive portion of the tool is in electrical contact with the patient. Thus, a surgeon may operate with monopolar electrosurgical tools from many different angles. In contrast, bipolar tools suffer from the drawback that the surgeon must carefully position the tool to ensure that both electrical poles are in electrical contact with the patient in order to apply electrosurgical current. This may limit the range of motion and the angle from which the surgeon can effectively use the bipolar tool.

However, with dry tip electrosurgical devices, both monopolar and bipolar, the temperature of tissue being treated may rise significantly higher than 100° C., possibly resulting in tissue desiccation, tissue sticking to the electrodes, tissue perforation, char formation and smoke generation.

One attempt with monopolar scissors, in order to restrict the electric current flow through the patient, has been to decrease the size of the active electrode to only a portion of the confronting (shearing) surfaces. In this manner, the chance that a surgeon may inadvertently conduct current into and burn surrounding tissue is also reduced. One such solution, as disclosed in U.S. Pat. No. 5,827,281 in the name of Levin entitled "Insulated Surgical Scissors," is to entirely cover the pair of opposing cutting blades with an electrically and thermally insulative material except along corresponding segments of the confronting surfaces. Thus, this '281 patent does not recognize any benefit to providing electrically active surfaces on the pair of opposing cutting blades other than certain segments of the confronting surfaces and aims to prevent such. However, the need for this insulative material also increases the complexity of the scissors.

However, the teachings of the U.S. Pat. No. 5,827,281 patent are somewhat in contrast to the U.S. Pat. No. 5,658,281 patent. The U.S. Pat. No. 5,658,281 patent discloses that it would be desirable to allow surgeons to use the exterior surfaces of the scissors to coagulate tissue. However, the U.S. Pat. No. 5,658,281 patent does not address how to reduce the burning of surrounding tissue addressed by the U.S. Pat. No. 5,827,281 patent, nor any other concerns of tissue desiccation, tissue sticking to the electrodes, coagulum build-up on the electrodes, tissue perforation, char formation and smoke generation which may occur with use of dry electrosurgical devices.

In light of the above, it is an object of the invention to provide devices, systems and methods which overcome the limitations of the art.

SUMMARY OF THE INVENTION

According to the present invention, radio frequency electrical power from a device is coupled to tissue through a coupling of fluid, also provided from the device, to inhibit such undesirable effects of tissue desiccation, sticking to the device, coagulum build-up on the device, tissue perforation, char formation and smoke generation. Specifically with regards to inhibiting tissue desiccation, one key factor is to inhibit the tissue temperature from exceeding 100° C. where the intracellular water may boil away, leaving the tissue extremely dry and much less electrically conductive.

According to one embodiment, electrosurgical scissors are provided comprising an end effector comprising a first blade member and a second blade member with the first blade member and the second blade member pivotally connected, an electrical connector configured to couple the scissors to a power source; and a fluid passage in fluid communication with at least one fluid outlet.

BRIEF DESCRIPTION OF THE DRAWINGS

To better understand and appreciate the invention, refer to the following detailed description in connection with the accompanying drawings, hand and computer generated.

DETAILED DESCRIPTION

Figure 1:
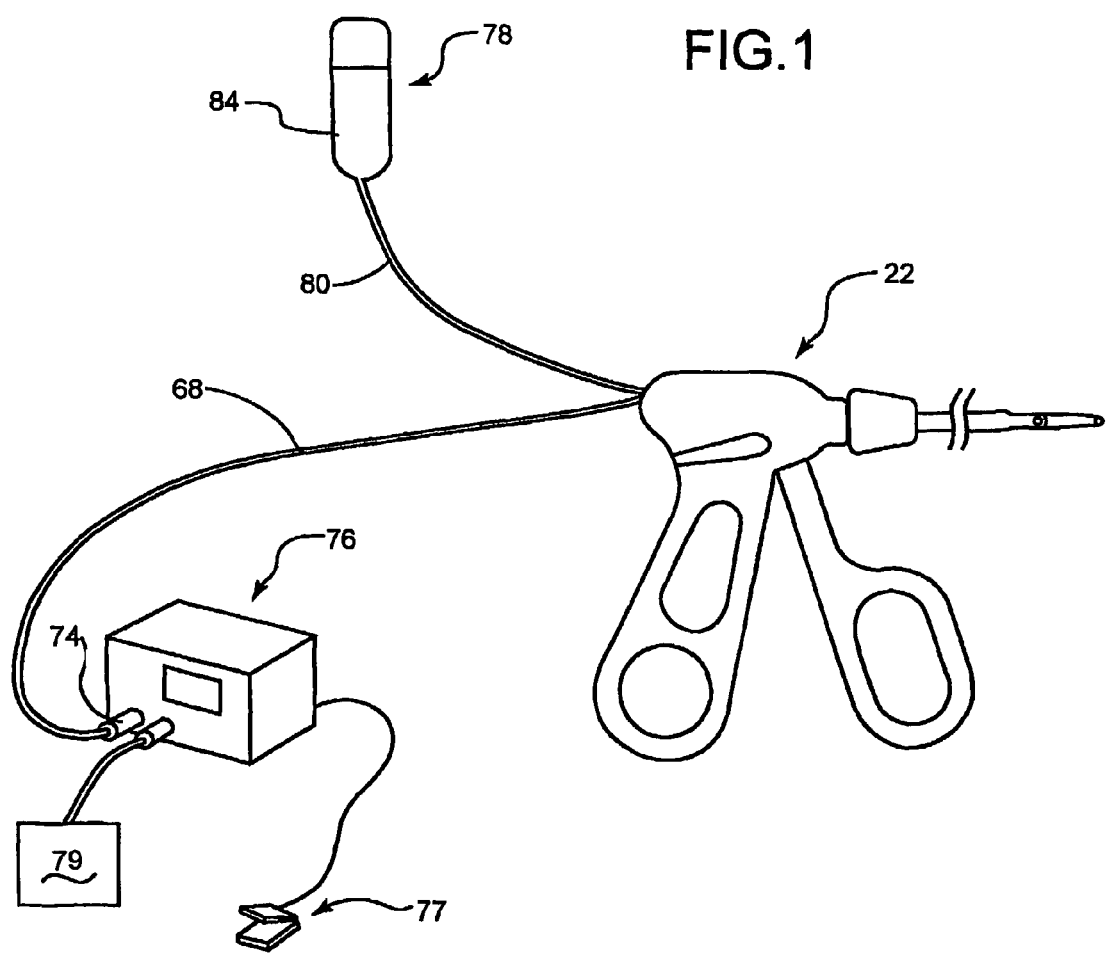
FIG. 1 is a schematic side view of an exemplary device as part of a system according to the present invention.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive. Also, from the specification, it should be clear that any use of the terms "distal" and "proximal" are made in reference to the user of the device, and not the patient.

An exemplary electrosurgical device according to the present invention will now be described in detail. The electrosurgical device may be used with the system of the invention to be described herein. However, it should be understood that the description of the combination is for purposes of illustrating the system of the invention only. Consequently, it should be understood that the electrosurgical device of the present invention can be used alone, or in conjunction with, the system of the invention. Conversely, it should be equally understood that the system of the present invention can be used with a wide variety of devices.

The electrosurgical devices disclosed herein may be configured for both open and laparoscopic surgery. For laparoscopic surgery, the devices are preferably configured to fit through either a 5 mm or 10 mm trocar cannula. When used in conjunction with a cannula, the devices disclosed herein eliminate the need to switch instruments from the cannula for the purposes of coagulating and cutting tissue.

An exemplary electrosurgical device of the present invention, which may be used in conjunction with one or more aspects of the system of the present invention, is shown at reference character 22 in FIG. 1. As shown, device 22 preferably comprises electrosurgical scissors, and more particularly laparoscopic electrosurgical scissors. When device 22 comprises laparoscopic electrosurgical scissors, preferably device 22 is configured to extend through a working channel of a trocar cannula.

Device 22 is designed and configured to coagulate and seal tissue from the flow of bodily fluids and/or air by shrinking the tissue (particularly collagen in the tissue and particularly vessels) and cut tissue. More specifically, device 22 can be painted over a raw, oozing surface of tissue to seal the tissue against bleeding, or focused on individual large vessels, such as to seal a bleeding vessel which has been cut or to occlude a vessel prior to its being cut.

As shown in FIG. 1, the system of the invention includes both a fluid source 78 and a power source 76 coupled to device 22 as discussed in greater detail below. As shown, fluid source 78 comprises an I.V. bag. The power source 76 shown in FIG. 1 preferably comprises a generator which provides alternating current, radio-frequency electrical energy at various rates (i.e. power). As to the frequency of the RF electrical energy, it is preferably provided within a frequency band (i.e. a continuous range of frequencies extending between two limiting frequencies) in the range between and including about 9 kHz (kilohertz) to 300 GHz (gigahertz). More preferably, the RF energy is provided within a frequency band in the range between and including about 50 kHz (kilohertz) to 50 MHz (megahertz). Even more preferably, the RF energy is provided within a frequency band in the range between and including about 200 kHz (kilohertz) to 2 MHz (megahertz). Most preferably, RF energy is provided within a frequency band in the range between and including about 400 kHz (kilohertz) to 600 kHz (kilohertz). The power from the power source 76 to device 22 is preferably turned on and off via a footswitch 77 or other easily operated switch connected to the power source 76.

Figure 2:
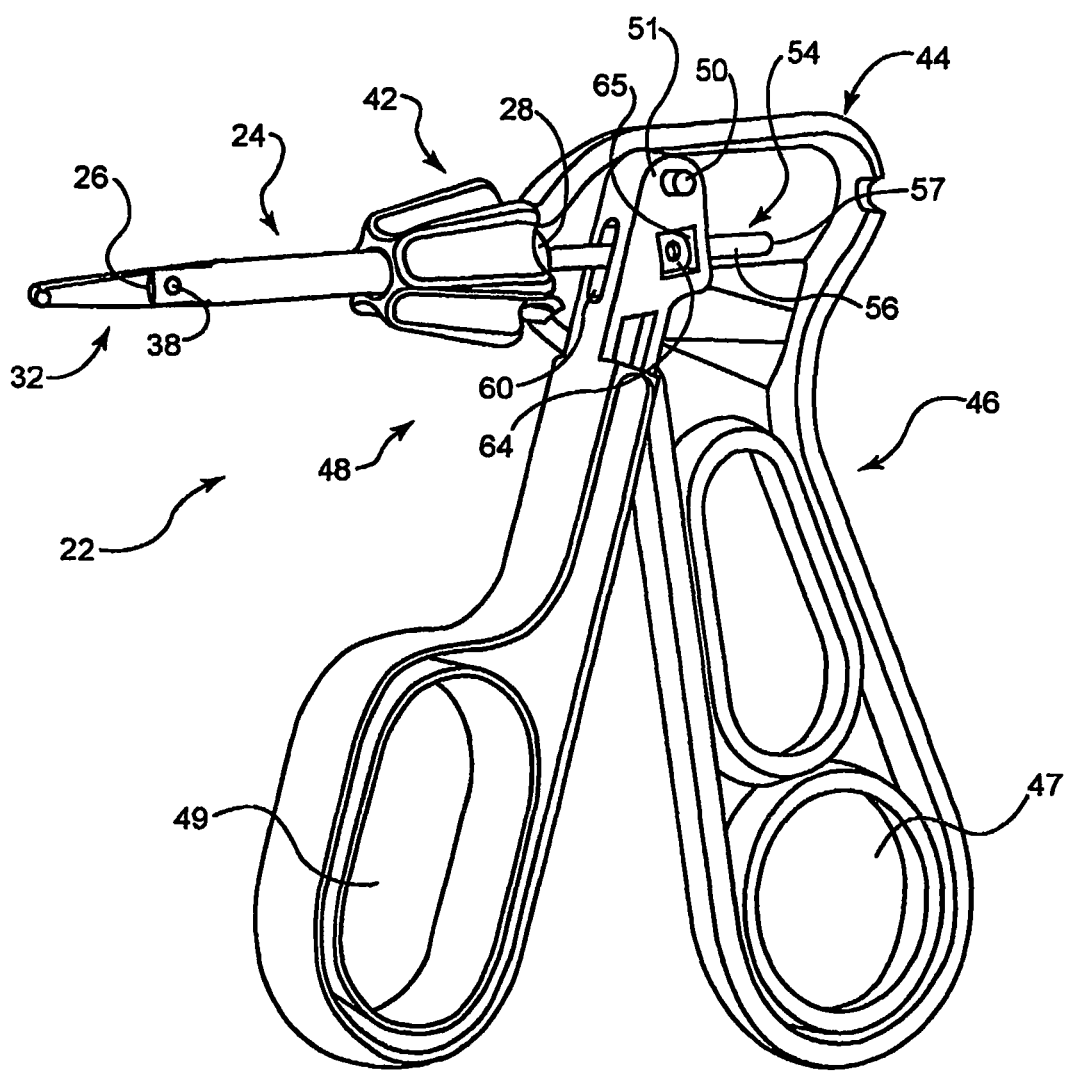
FIG. 2 is a schematic isometric view of the device shown in FIG. 1 with a portion of the handle removed.
Figure 3:
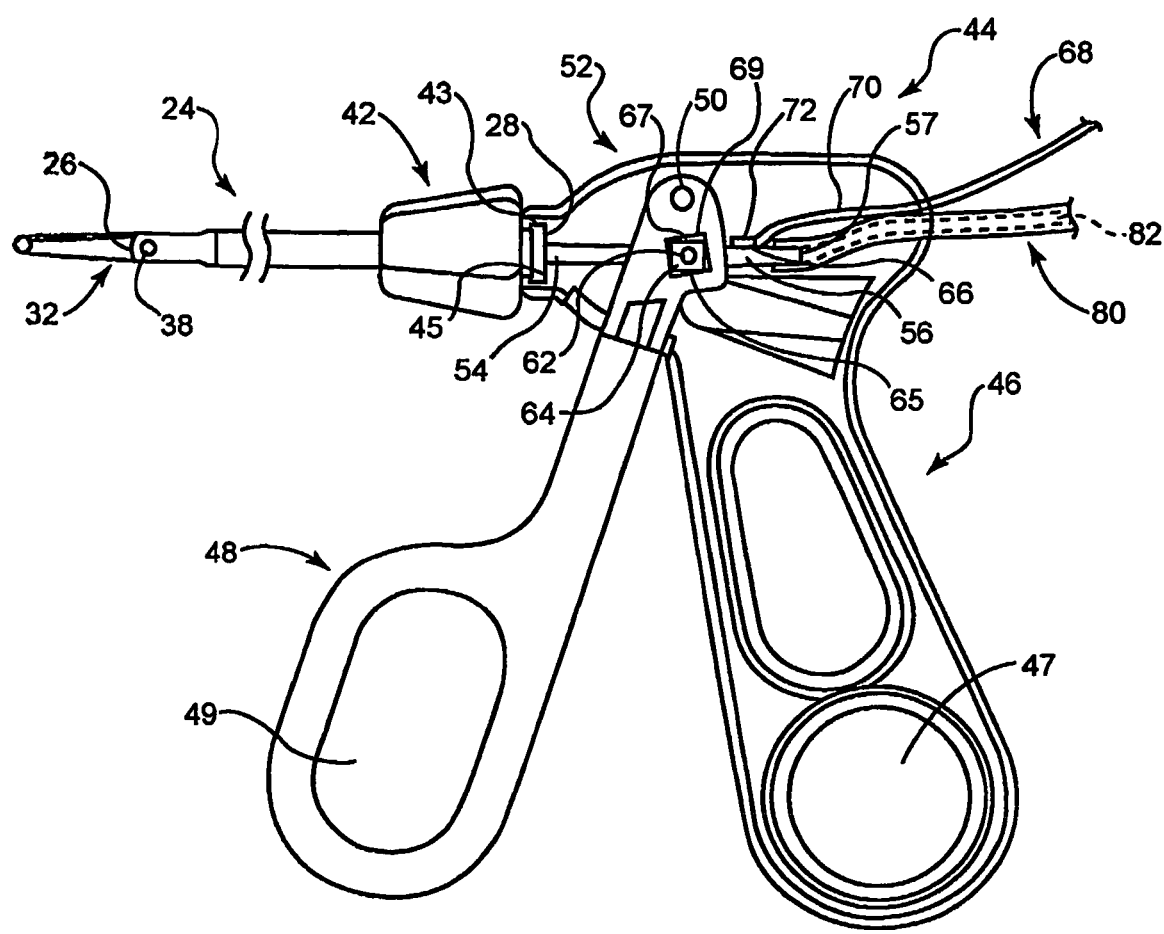
FIG. 3 is a schematic side view of the device shown in FIG. 2 with power cable and fluid line connected to the device.
Figure 7:
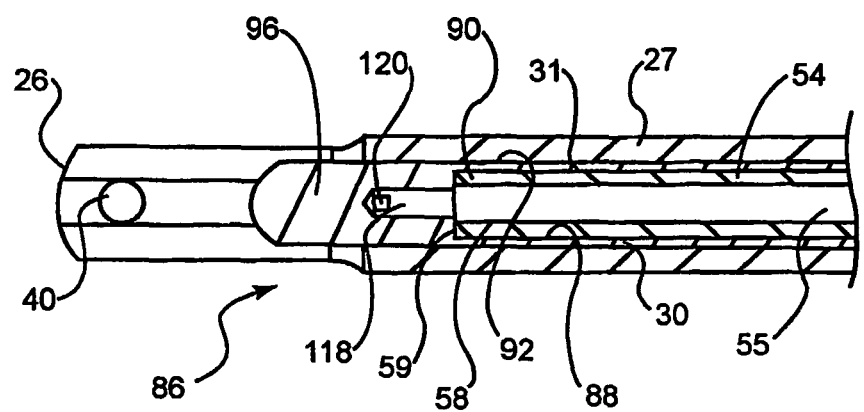
FIG. 7 is a schematic, close-up, cross-sectional side view of a distal portion of the device shown in FIG. 6.

As best shown in FIGS. 2 and 3, device 22 preferably includes an intermediate portion comprising an elongated, hollow, electrically insulated, rigid shaft 24 having a distal end 26, a proximal end 28 and a central lumen 30 (shown in FIG. 7). While shown greatly shortened as indicated by the break lines, the length of shaft 24 is preferably in the range between and including about 5 inches to 15 inches.

Figure 4:
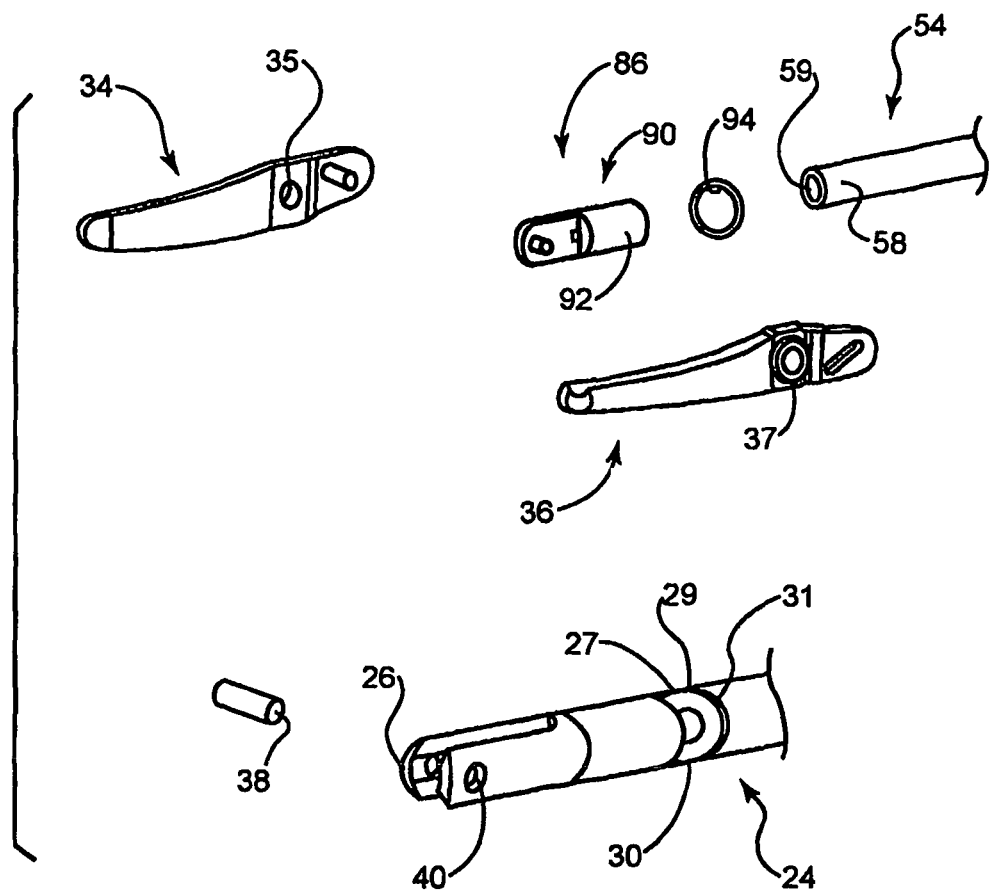
FIG. 4 is a schematic, close-up, exploded isometric view of a distal portion of the device shown in FIG. 3.

As best shown in FIG. 4, for strength purposes, shaft 24 preferably comprises an inner, cylindrical metal tube 27, such as stainless steel, with the outer layer 29 of insulating material applied thereon, such as a polymer, ceramic or glass material. Where the outer layer 29 comprises a polymer, preferably the outer layer is provided in the form of a shrink wrap sleeve which may be heated and thereafter shrunk directly onto the metal tube 27 in a manner known in the art. In other embodiments, cylindrical tube 27 may comprise an electrically insulating material itself, such as a polymer, ceramic or glass material, thus eliminating the need for outer layer 29.

Figure 5:
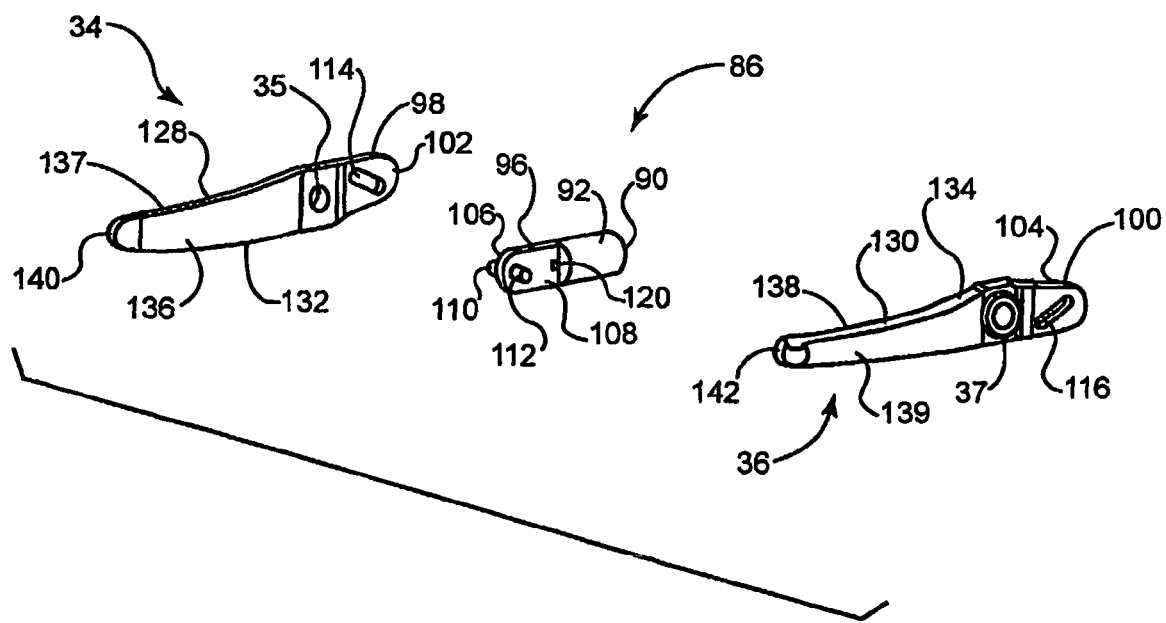
FIG. 5 is another schematic, close-up, exploded isometric view of a distal portion of the device shown in FIG. 3.

Also as shown in FIGS. 2 and 3, device 22 also preferably includes an end effector 32. As best shown in FIGS. 4 and 5, end effector 32 comprises two cooperating, relatively moveable blade members 34, 36. Blade members 34, 36 extend distally from and are pivotally coupled adjacent the distal end 26 of the shaft 24 such that they hinge about a pivot 38 provided, for example, by a separate metal pin, extending through a fixed pivot hole 40 of shaft 24 and aligning holes 35, 37 in the blade members 34, 36.

Returning to FIGS. 2 and 3, device 22 also preferably includes a collar 42 for rotating the entire shaft 24 and end effector 32 relative to a proximal handle 44 comprising an electrically insulated first handle member 46 and an electrically insulated second handle member 48, which are coupled adjacent the proximal end 28 of shaft 24. As shown in FIGS. 2 and 3, a mirrored half of the first handle member 46, which is preferably formed from two separately formed mating pieces, has been removed to expose the inner workings of the handle 44. The first and second handle members 46, 48 are preferably made electrically insulating by virtue of being molded of an electrically insulating polymer material.

First handle member 46 is preferably coupled to the proximal end 28 of the shaft 24 by means a circular flange lip 43 of the shaft 24 contained within a mating and interlocking circular recess 45 formed in the first handle member 46, while the second handle member 48 is pivotally coupled to the first handle member 46 about a pivot 50 provided, for example, by a pin. The second handle member 48 is indirectly coupled to the blade members 34, 36 through a push/pull rod assembly 52 extending through the lumen 30 of the elongated shaft 24 so that axial reciprocal movement of the push/pull rod assembly 52 relative to shaft 24 opens and closes the blade members 34, 36. In this manner, shaft 24 functions as a guide barrel for the rod 54 of the push/pull rod assembly 52.

Figure 6:
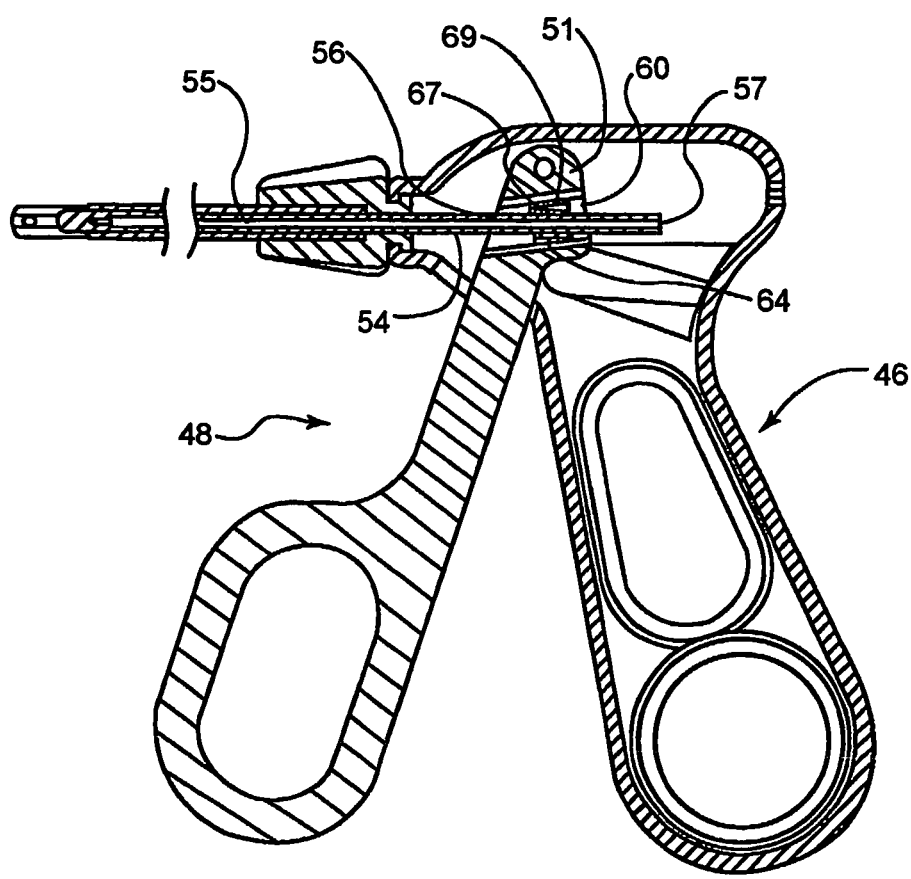
FIG. 6 is a schematic, cross-sectional side view of the device shown in FIG. 2 with the blade members removed.

As best shown in FIGS. 2 and 6, a proximal portion 56 of a rod 54 extends through a longitudinally orientated (i.e. extending proximally and distally with respect to device 22) slotted receptacle 60 extending through a head portion 51 of second handle member 48. Returning to FIG. 3, rod 54 is preferably coupled to second handle member 48 such that the position of rod 54 relative to the position of the second handle member 48 may be adjustably fixed thereto (e.g. to accommodate manufacturing). As shown, rod 54 is coupled to the second handle member 48 by a mechanical fastener 62 comprising here, for example, a set screw. However, rather than threading the screw into a threaded hole in handle 48 and into contact with the rod 54, preferably the set screw 62 is threaded into the side wall of metal sleeve 64. In this manner the strength of the threaded connection is substantially increased with less likelihood of stripping threads. Screw 62 is preferably treaded through the side wall of sleeve 64 such that the distal end surface of the set screw 62 engages and locks against a side surface of the rod 54 intersecting the threaded hole in the sleeve 64.

As shown in FIGS. 2 and 3, once sleeve 64 is fixed to rod 54, the sleeve 64 is than coupled to handle 48 by being located in a fastener or sleeve interlocking receptacle 65. As receptacle 65 moves proximally and distally with the movement of handle 48, the surfaces of the receptacle accordingly act on the opposing surfaces of the sleeve 64 to move the sleeve 64 and fixed rod 54 in unison with the handle 48.

In addition, rod 54 is also preferably pivotally coupled to the second handle member 48 about a pivot connection, provided here, for example, by the sleeve 64 and receptacle 65 interaction. As shown in FIGS. 3 and 6, certain surfaces 69 of receptacle 65 are spaced from interacting surfaces 67 of the sleeve 64 to allot for limited pivotal movement between sleeve 64 and receptacle 65.

Continuing with FIG. 3, the grasping first handle member 46 also provides a pistol grip configuration while second handle member 48 provides a trigger or lever configuration. Also as shown, first handle member 46 is provided with a thumb loop 47 while second handle member 48 is provided with a finger loop 49 for easier grasping and manipulation of device 22. With the configuration shown, as the first and second handle members 46, 48 are moved towards one another, rod 54 is moved proximally to close the blade members 34, 36 relative to one another. Conversely, when the first and second handle members 46, 48 are moved apart from one another, rod 54 is moved distally to open the blade members 34, 36 relative to one another.

As shown in FIGS. 1 and 3, device 22 is preferably connected to a power source 76 (shown in FIG. 1) via proximal portion 56 of rod 54. As shown, to provide power to device 22, an electrical connection to a power source 76 is preferably provided with a cable 68. As shown in FIG. 3, cable 68 comprises an insulated wire 70, comprising a wire conductor 72, and a plug 74 (shown in FIG. 1). With regards to the electrical connection, rod 54 is coupled to one end of cable 68 by a soldered connection 66 while the other end of the cable 68 is coupled to power source 76 with plug 74 inserted into a plug receptacle of the power source 76.

With the above configuration, device 22 may be electrically energized for coagulating and cutting tissue to be discussed in greater detail herein. As constructed, electrical power provided to rod 54 from power source 76, which may be referred to as the active terminal, will also flow to blade members 34, 36 by virtue of their mechanical and metallic coupling to the rod 54, as well as tube 27 of shaft 24. Thus, the device 22 comprises a monopolar configuration, i.e., electrical power is delivered from the power source 76 via a single conductor 72 to each of the blade members 34, 36 (each comprising a metal such as titanium or stainless steel), with both blade members consequently being at substantially the same voltage or electrical potential. The return for the electrical energy from device 22 is through the patient (not shown) generally to a large surface, electrically dispersive ground pad 79 (shown in FIG. 1), often referred to as the return or indifferent terminal, located on the patient, typically on the back or other suitable anatomical location, and then back to the power source 76, as is well-known in the art.

Continuing with FIGS. 1 and 3, device 22 is preferably connected to a fluid source 78 (shown in FIG. 1) also via proximal portion 56 of rod 54. As shown, to provide fluid 84 to device 22, a fluid connection to a fluid source 78 is preferably provided with an input fluid line 80. As shown in FIG. 3, input fluid line 80 comprises a flexible fluid line made from a polymeric material, such as polyvinylchloride (PVC) or polyolefin (e.g. polypropylene, polyethylene) and has a fluid passage 82 (lumen). With regards to the fluid connection, rod 54 is coupled to one end of fluid line 80 by interference fitting the lumen 82 of the input fluid line 80 over the proximal end 57 and outside diameter of rod 54 to provide a press fit seal there between. Additionally an adhesive may be disposed there between to strengthen the seal. The other end of input fluid line 80 may be directly connected to fluid source 78.

Fluid source 78 preferably provides an electrically conductive fluid 84, which preferably is a saline solution and, more preferably sterile, physiologic saline. It should be understood that where description herein references the use of saline as the fluid 84, other electrically conductive fluids can be used in accordance with the invention.

For example, in addition to the conductive fluid comprising physiologic saline (also known as "normal" saline, isotonic saline or 0.9 weight-volume percentage sodium chloride (NaCl) solution), the conductive fluid may comprise hypertonic saline solution, hypotonic saline solution, Ringers solution, lactated Ringer's solution, Locke-Ringer's solution, or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

In certain embodiments as discussed herein, hypertonic saline, saturated with NaCl to a concentration of about 15% (weight-volume percentage), may be preferred to physiologic saline to reduce the electrical resistivity of the saline from about 50 ohm-cm at 0.9% to about 5 ohm-cm at 15%. This ten-fold reduction in electrical resistivity of the conductive fluid will enhance the reduction in heating (both resistance heating and conduction heating) of tissue and the conductive fluid itself as shown herein.

While a conductive fluid is preferred, as will become more apparent with further reading of this specification, the fluid 84 may also comprise an electrically non-conductive fluid. The use of a non-conductive fluid is less preferred to that of a conductive fluid as the non-conductive fluid does not conduct electricity. However, the use of a non-conductive fluid still provides certain advantages over the use of a dry electrode including, for example, reduced occurrence of tissue sticking to the blade members 34, 36, cooling of tissue and/or the blade members 34, 36, and removal of any coagula, if existent, from the blade members 34, 36 and/or the tissue treatment site. Therefore, it is also within the scope of the invention to include the use of a non-conducting fluid, such as, for example, deionized water. Other non-conductive fluids include 5% w/v dextrose injection USP and 10% w/v dextrose injection USP (i.e. sterile solutions of 5 g and 10 g dextrose hydrous in 100 ml water, respectively); 1.5% w/v glycine irrigation USP (i.e. sterile solution of 1.5 g glycine in 100 ml water); 5% w/v, 10% w/v, 15% w/v and 20% w/v mannitol injection USP (i.e. sterile solution of 5 g, 10 g, 15 g and 20g mannitol in 100 ml water, respectively); 3% sorbitol irrigation USP (i.e. sterile solution of 3 g sorbitol in 100 ml water); 0.54% sorbitol/2.75% mannitol irrigation USP (i.e. sterile solution of 0.54 g sorbitol and 2.75 g mannitol in 100 ml water); and sterile water for irrigation USP.

Once the input fluid line 80 is coupled to rod 54, the fluid passage 82 provided by fluid line 80 is now fluidly coupled to fluid passage 55, here provided by the bore or lumen, of rod 54 (shown in FIGS. 6 and 7). In this manner fluid 84 from fluid source 78 may flow towards the distal end of device 22.

As best shown in FIGS. 4 and 7, the distal end 59 of rod 54 is preferably coupled to a connector member 86. More specifically, as shown in FIG. 7, a distal portion 58 of rod 54 is interference fit (pressed) into rod connector portion comprising a circular receptacle portion 88. Alternatively, the outer side wall of distal portion 58 of rod 54 may be provided with external threads configured to mate with internal threads contained on the inner side wall of receptacle portion 88.

Continuing with FIGS. 4 and 7, a circular portion 90 of connector member 86 is configured to have an outer diameter slightly smaller (e.g. about 0.001 inches to 0.040 inches) than the inner diameter of tube 27. In this manner, outer circular surface 92 of connector member 86 may easily slide along inner surface 31 of tube 27 with the reciprocal movement of rod 54 while, at the same time, receptacle portion 88 of connector member 86 is able to position the distal portion 58 of rod 54 towards the center of tube 27. In order to inhibit the back flow of fluid 84 (which has been provided from device 22 to a tissue treatment site or by virtue of the orientation of device 22 with the distal end positioned above the proximal end) into lumen 30, preferably the outer diameter of the circular portion 90 fits with the inner surface 31 of tube 27 to substantially seal the lumen 30 of tube 27 and handle 44 against the back flow of fluid 84 therein. In order to increase the seal, a separate seal member 94 (shown in FIG. 4) may be placed between surfaces 92 and 31, such as a flexible O-ring gasket. Alternatively, the O-ring gasket may be located near between a proximal portion 56 of rod 54 and a proximal portion of shaft 24.

As best shown in FIG. 5, located distally from receptacle portion 88, connector member 86 comprises a blade member connector portion 96, which has a substantially planar tongue extending distally relative to the circular receptacle portion 88, and which is sandwiched between and spaces apart the proximal portions 98, 100 of blade members 34, 36 respectively. As shown, flat interior surfaces 102, 104 of blade members 34, 36, which face one another, overlie opposing flat surfaces 106, 108 of blade member connector portion 96.

Continuing with FIG. 5, blade member connector portion 96 includes opposing pins 110, 112 extending laterally from opposing surfaces 106, 108. Pins 110, 112 are configured to fit within and travel along the slotted recesses 114, 116 in surfaces 102, 104 of blade members 34, 36 to open and close blade members 34, 36 relative to each other. More specifically, as pins 110, 112 move proximally while in recesses 114, 116 (due to proximal movement of rod 54), blade members 34, 36 rotate in opposing directions relative to each other around pivot 38 and close relative to one another. Conversely, as pins 110, 112, move distally while in recesses 114, 116 (due to distal movement of rod 54), blade members 34, 36, which still rotate in opposing directions relative to each other, now rotate in opposing directions to their closing directions around pivot 38, to open relative to one another. As shown, in order to facilitate the opening and closing movement of blade members 34, 36, the orientation of recesses 114, 116 is such that they are orientated in opposing directions relative to one another.

In order to expel fluid 84 which has flowed distally in lumen 55 of rod 54 from device 22, the connector member 86 is preferably provided with one or more apertures in fluid communication with lumen 55, the apertures providing a fluid outlet for fluid 84. As best shown in FIG. 7, the bottom wall of receptacle portion 88 includes an aperture 118 there through to provide a fluid outlet 120 for fluid 84. As shown in FIG. 7, fluid outlet 120 is located proximal to the distal end 26 of shaft 24 such that it is remote from the tissue interacting portions of blade members 34, 36. Stated another way, fluid outlet 120 is recessed and protected within the distal end 26 of shaft 24 which provides a location substantially inaccessible to direct contact or occlusion with tissue. While only a single fluid outlet 120 is shown, it should be understood that additional fluid outlets (with varying locations) may be similarly incorporated to the extent necessary.

Figure 8:
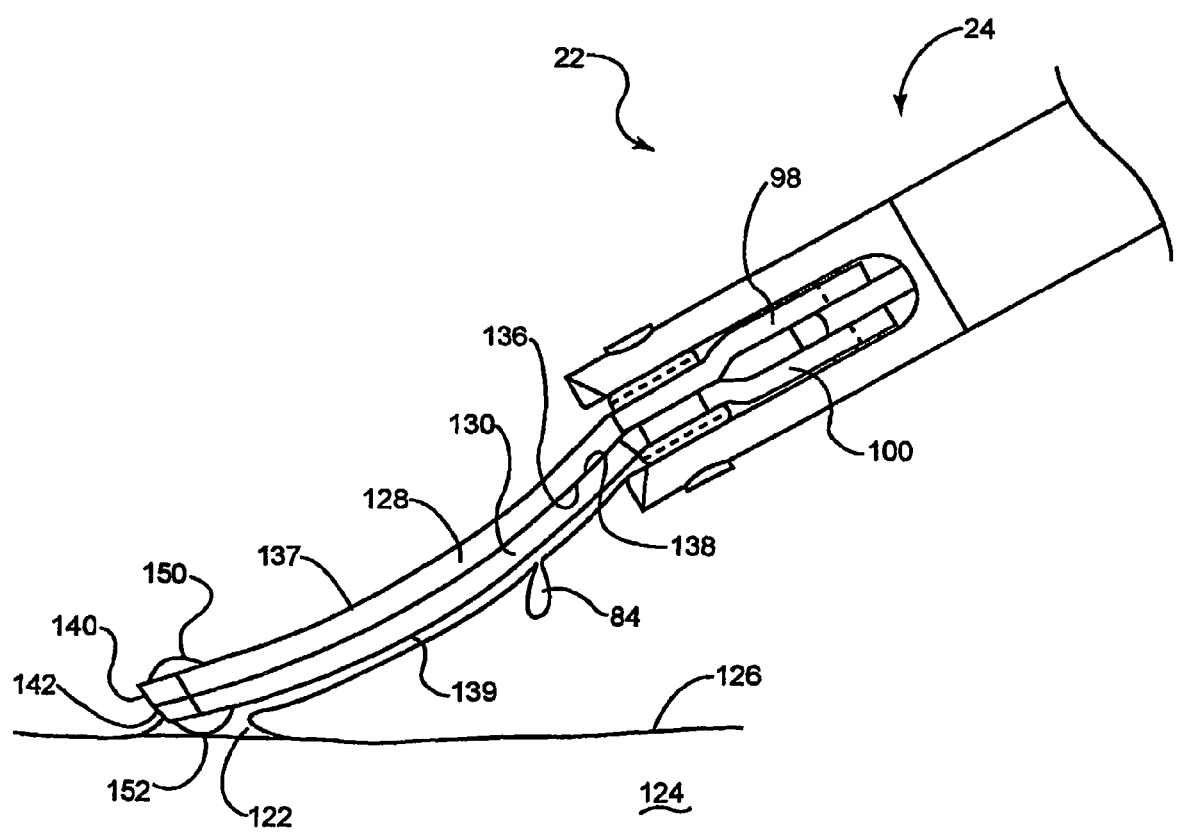
FIG. 8 is a schematic, close-up, top view of a distal portion of the device shown in FIG. 2 in the presence of tissue.

As shown in FIG. 8, during use of device 22 for coagulating tissue, a fluid coupling 122, preferably comprising a discrete localized web, provides a film of fluid 84 between the surface 126 of the tissue 124 and blade members 34, 36. When a user of device 22 places the blade members 34, 36 at a tissue treatment site and moves the blade members 34, 36 across the surface 126 of the tissue 124, fluid 84 is simultaneously expelled from fluid outlet 120 around and onto the proximal portions 98, 100 and to the distal portions 128, 130 of blade members 34, 36 and thereafter onto the surface 126 of tissue 124 via fluid coupling 122. The fluid 84 flows from the distal end of connector 86 towards the distal portions 128, 130 and ends 140, 142 of blade members 34, 36 due to the force of gravity, and the orientation of the device 22, which is almost always with the distal end downward. Surface tension forces tend to keep the fluid 84 from dripping off the blade members 34, 36 before the fluid 84 reaches the distal ends 140, 142 of blade members 34, 36 and the contact with tissue 124.

Fluid 84 lubricates the surface 126 of the tissue 124 and facilitates the movement of blade members 34, 36 across the surface 126 of the tissue 124 and, in the instance of an electrically conductive fluid, provides an electrical coupling between the device 22 and the tissue 124. During movement of the blade members 34, 36, the user of device 22 typically slides the blade members 34, 36 across the surface 126 of the tissue 124 back and forth with a painting motion while using the fluid 84 as, among other things, a lubricating coating. Preferably the thickness of the fluid coupling 122 between the blade members 34, 36 and the surface 126 of the tissue 124 is in the range between and including about 0.05 mm to 2.5 mm. More preferably, the fluid coupling 122 between the blade members 34, 36 and the surface 126 of the tissue 124 is in the range between and including about 0.1 mm to 1.0 mm.

Preferably tissue coagulation is performed with blade member exterior side surfaces 137, 139 of blade members 34, 36 which oppose blade member interior side shearing surfaces 136, 138, respectively. As shown in FIG. 8, in order to better facilitate sliding of device 22 on the surface 126 of tissue 124, preferably the distal portions 128, 130 of blade members 34, 36 proximally adjacent distal ends 140, 142 may each comprise opposing bulbous portions, here having preferably smooth (i.e. devoid of edges), semi-circular surfaces 150, 152 (preferably of about 180 degrees and having a surface finish in the range between and including about 16-64 microinches RMS (Root Mean Square)) provided by enlarged semi-circular regions. Consequently, when blade members 34, 36 are closed together, the two opposing semi-circular regions may provide a spherical distal end tip for device 22. In this manner, the distal end surface area of device 22 is increased to provide an appropriate power density for coagulating tissue with a painting motion. For example, for a power level of 50 watts, which is a typical upper limit for most laparoscopic procedures, a spherical cross-sectional dimension, here diameter, in the range of between and including about 2 to 2.5 millimeters has been found to work best. If the power can be as high as 100 watts, then the dimension should be larger, in the range of between and including about 3 to 4 millimeters. If the power is smaller, for instance 25 watts, then the dimension should be smaller, in the range between and including about 1.25 to 1.75 millimeters. Furthermore, in order to further facilitate tissue coagulation, preferably the distal portions 128, 130 of blade members 34, 36 are arcuate to provide a convex surface 139 of blade member 36 which may be more easily positioned against tissue and slide there along.

When electric current is applied to blade members 34, 36, heating of the tissue 124 occurs by means of electrical resistance heating. In other words, increasing the temperature of the tissue 124 as a result of electric current flow through the tissue, with the associated electrical energy being converted into thermal energy (i.e. heat) via accelerated movement of ions as a function of the tissue's electrical resistance. Resistance heating provides direct, instantaneous heating inside tissue 124 due to the current flow through tissue 124.

Device 22 is particularly useful to a surgeon who wishes to coagulate and seal tissue, including vessels such as blood vessels, prior to tissue 124 being cut with blade members 34, 36. More specifically, as blade members 34, 36 are moved along the surface 126 of tissue 124, tissue 124 there beneath is coagulated. As known in the art, when exposed to heat, the collagen of the blood vessels will shrink, thus decreasing the diameter and associated lumen of the vessel. Certain vessels, depending on size and proximity to surface 126 of tissue 124 will become completely occluded (e.g. vessels up to about 1 mm in diameter and 1-5 mm deep), while vessels greater than 1 mm may become only partially occluded and need additional treatment with another device, such as a clip applier, or with suture ligation. Some vessels, such as those 1 mm diameter or less, may not be initially sealed because they are too deep in the tissue, but these may be occluded as the device 22 is used to coag and cut deeper into the tissue.

Once surface 126 of tissue 124 is adequately treated with device 22, at least one of the distal ends 140, 142 of blade members 34, 36 may be used to pierce and perforate tissue 124, such as through the capsule of a liver. Preferably, the depth of the perforation is no deeper than the depth of tissue treatment provided by the surface coagulation to avoid possible puncturing of an untreated vessel. After making the first perforation in tissue 124, a second perforation laterally spaced from the first perforation may be made, also into treated tissue 124. Thereafter, the portion of tissue 124 between the first and second perforations may be located between shearing edges 132, 134 and shearing surfaces 136, 138 and thereafter cut when blade members 34, 36 are closed together. In alternative embodiments, both perforations may be made simultaneously with distal ends 140, 142 of blade members 34, 36. In still other embodiments, only one perforation made may made. In this manner one blade member 34 may be located in the perforation while the distal end 142 of the other blade member 36 is laterally spaced and pressed against the surface 126 of tissue 124 to cut the tissue 124 when blade members 34, 36 are closed together. In still other embodiments, no perforations of tissue 124 may be required prior to cutting as where tissue 124 may be manipulated and located between the shearing edges 132, 134 and shearing surfaces 136, 138 of open blade members 34, 36 without the need for the perforations.

It should be noted that, as shown, preferably distal ends 140, 142 of blade members 34, 36 are blunt. In other words distal ends 140, 142 of blade members 34, 36 preferably do not comprise a distal end point. The distal ends 140, 142 of blade members 34, 36 preferably are not pointed so that the distal ends 140, 142 of blade members 34, 36 will slide along the tissue surface 126 while the blade members 34, 36 are moved along the tissue surface 126 with a back and forth painting motion, and while tissue coagulation is performed with blade member exterior side surfaces 137, 139 of blade members 34, 36.

In the instance of parenchyma tissue, such as for liver, the distal end 140, 142 of one or both of blade members 34, 36 may be used to simultaneously blunt dissect and coagulate tissue without first perforating the tissue 124. As the surface 126 of tissue 124 is coagulated under and around the at least one of the blade members 34, 36, the blade member may then be used to blunt dissect into the coagulated parenchyma, with the distal ends 140, 142. As the device 22 enters an elongated crevice in the surface 126 of the tissue 124 formed by the blunt dissection, shearing edges 132, 134 of blade members 34, 36 may be used to further blunt dissect the coagulated parenchyma on the sidewalls of the crevice, or blunt dissect and coagulate simultaneously. Blunt dissection of the coagulated parenchyma is performed by continuous abrading or splitting apart of the parenchyma with the substantially the same back and forth motion as coagulation of the surface 126 of the tissue 124. However, with blunt dissection, the surgeon typically applies more force to the tissue. In various embodiments, once the parenchyma is coagulated, blunt dissection may be performed with or without the radio frequency power (i.e. on or off) and/or with or without the presence of fluid 84.

In yet another technique, blade members 34, 36 may be used for wedge dissection. In other words, while blade members 34, 36 are in the closed position and without tissue 124 there between, they are wedged into tissue 124, preferably between adjacent tissue planes. Thereafter, the blade members 34, 36 may be slowly opened and, due to the separation forces placed on the tissue 124 at the distal ends 140, 142 of the blade members 34, 36, the tissue will dissect.

The above techniques can also be used on other parenchymal organs such as the pancreas, the kidney, and the lung. In addition, it may also be useful on muscle tissue and subcutaneous fat. Its use can also extend to benign tumors, cysts or other tissue masses found in the urological or gynecological areas. It would also enable the removal of highly vascularized tumors such as hemangiomas.

The use of the disclosed devices can result in significantly lower blood loss during surgical procedures such as liver resections. Typical blood loss for a right hepatectomy can be in the range of 500-1,000 cubic centimeters. Use of the devices disclosed herein to perform pre-transection coagulation of the liver can result in blood loss in the range of 50-300 cubic centimeters. Such a reduction in blood loss can reduce or eliminate the need for blood transfusions, and thus the cost and negative clinical consequences associated with blood transfusions, such as prolonged hospitalization and a greater likelihood of cancer recurrence. Use of the device can also provide improved sealing of bile ducts, and reduce the incidence of post-operative bile leakage, which is considered a major surgical complication.

In addition to liver resections, device 22 may be particularly useful to a surgeon performing a laparoscopic cholecystectomy (abbr. "lap chole") for the case of, for instance, either acute cholecystitis or an intrahepatic gallbladder in that the device provides multi-functional uses. More particularly, device 22 is useful to the surgeon for coagulation and dissection of an inflamed serosal layer of tissue 124 between the liver and gallbladder, which may include tough, fibrous, highly vascular connecting tissue between the organs.

The power provided from the surgical device 22 is generally in the range between and including about 20 watts to 150 watts, and more preferably in the range between and including about 50 watts to 100 watts. The fluid provided from the surgical device 22 is generally in the range between and including about 1 cubic centimeter per minute to 100 cubic centimeters per minute, and more preferably in the range between and including about 5 cubic centimeter per minute to 25 cubic centimeters per minute. For a more complete discussion of an exemplary power to fluid flow rate relationship see U.S. Publication No. 2002/0062123 in the name of McClurken entitled "Fluid-Assisted Medical Devices, Fluid Delivery Systems And Controllers For Such Devices, And Methods" published May 23, 2002.

In order to minimize the sticking of tissue, particularly coagulum, to blade members 34, 36, but yet adequately heat the tissue for treatment, preferably the temperature of the tissue should remain in the range between and including about 75° C. to 120° C. As known in the art, tissue containing Type I collagen (e.g., walls of blood vessels, bronchi, bile ducts, etc.) shrinks when exposed to about 85° C. for an exposure time of 0.01 seconds, or when exposed to about 65° C. for an exposure time of 15 minutes. An exemplary target temperature/time for tissue shrinkage is about 75° C. with an exposure time of about 1 second. More generally, the power provided to the tissue should be sufficient to shrink collagen in the range between and including about 1 second to 10 seconds after RF activation. An exemplary method of controlling the tissue temperature below 120° C. is to remove excess heat generated in the tissue by means of fluid 84, particularly by boiling the fluid coupling 122. Where fluid 84 comprises saline, the fluid 84 boils at approximately 100° C. to remove heat from the tissue and inhibit the tissue temperature from exceeding 100° C. For a more detailed discussion, see U.S. Publication No. 2002/0062123 in the name of McClurken as identified above.

Figure 9:
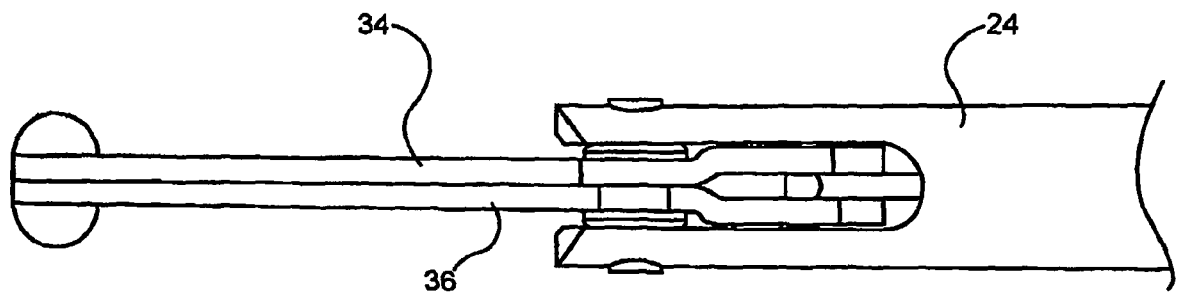
FIG. 9 is a schematic, close-up, top view of a distal portion of an alternative embodiment of the device of FIG. 2.

Thus far the device 22 has been described relative to use with scissors with curved blade members 34, 36. In still other embodiments, as shown in FIG. 9, the device of the present invention may comprise straight blade members 34, 36.

Figure 10:
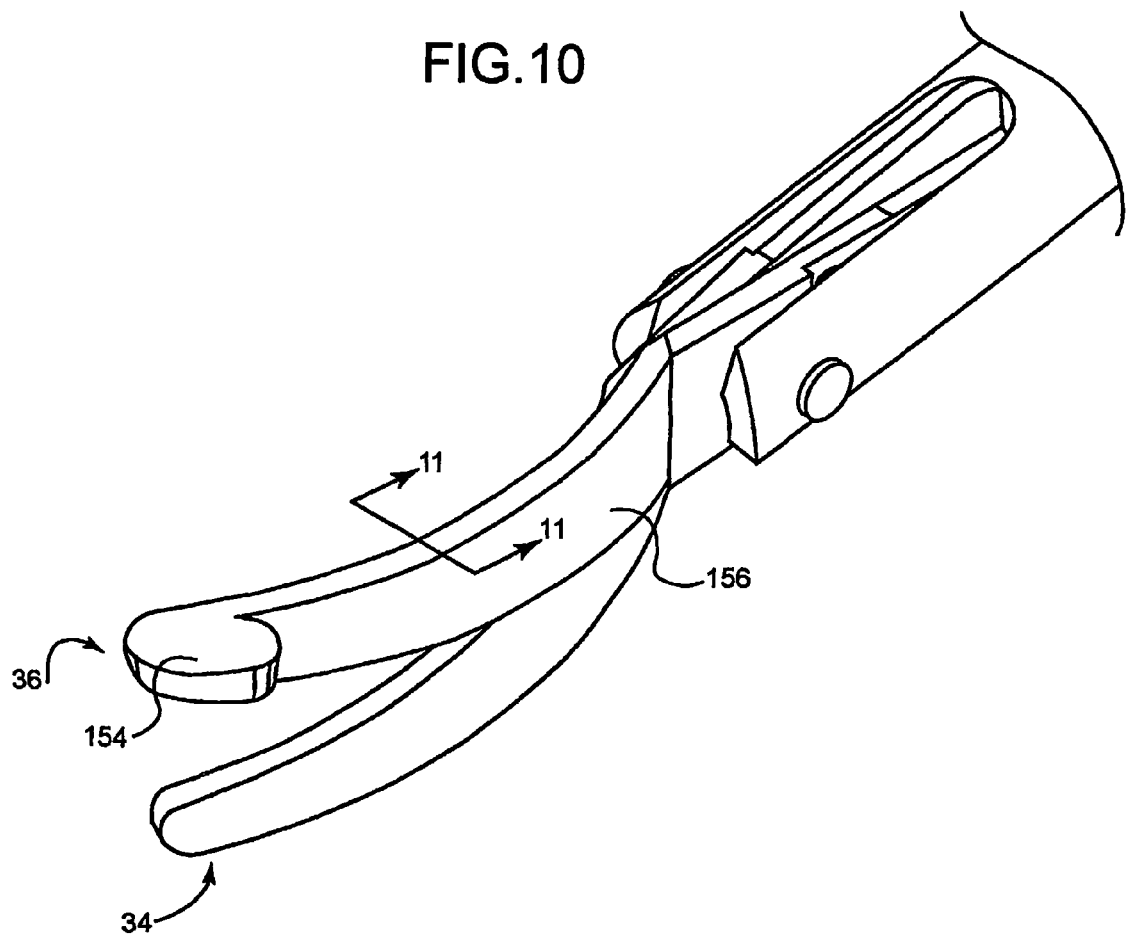
FIG. 10 is a schematic, close-up, isometric view of a distal portion of another alternative embodiment of the device of FIG. 2.

In yet another embodiment as shown in FIG. 10, only blade members 36 of electrosurgical device 22 has a bulbous portion 154, thus providing an asymmetric tip. Also different from previous embodiments, as shown the exterior side surfaces 137, 139 of blade members 34, 36 include a covering 156 of electrically insulating material, such as a polymer, ceramic or glass, except for the surface 152 of bulbous portion 154. An exemplary polymer comprises fluorine and, more particularly, polytetrafluoroethylene. In this manner, electrical current from blade members 34, 36 may be concentrated into tissue through bulbous portion 154. From the above description it should be understood that in other embodiments, covering 152 may also be used when neither of blade members 34, 36 include a bulbous portion 154.

Figure 11:
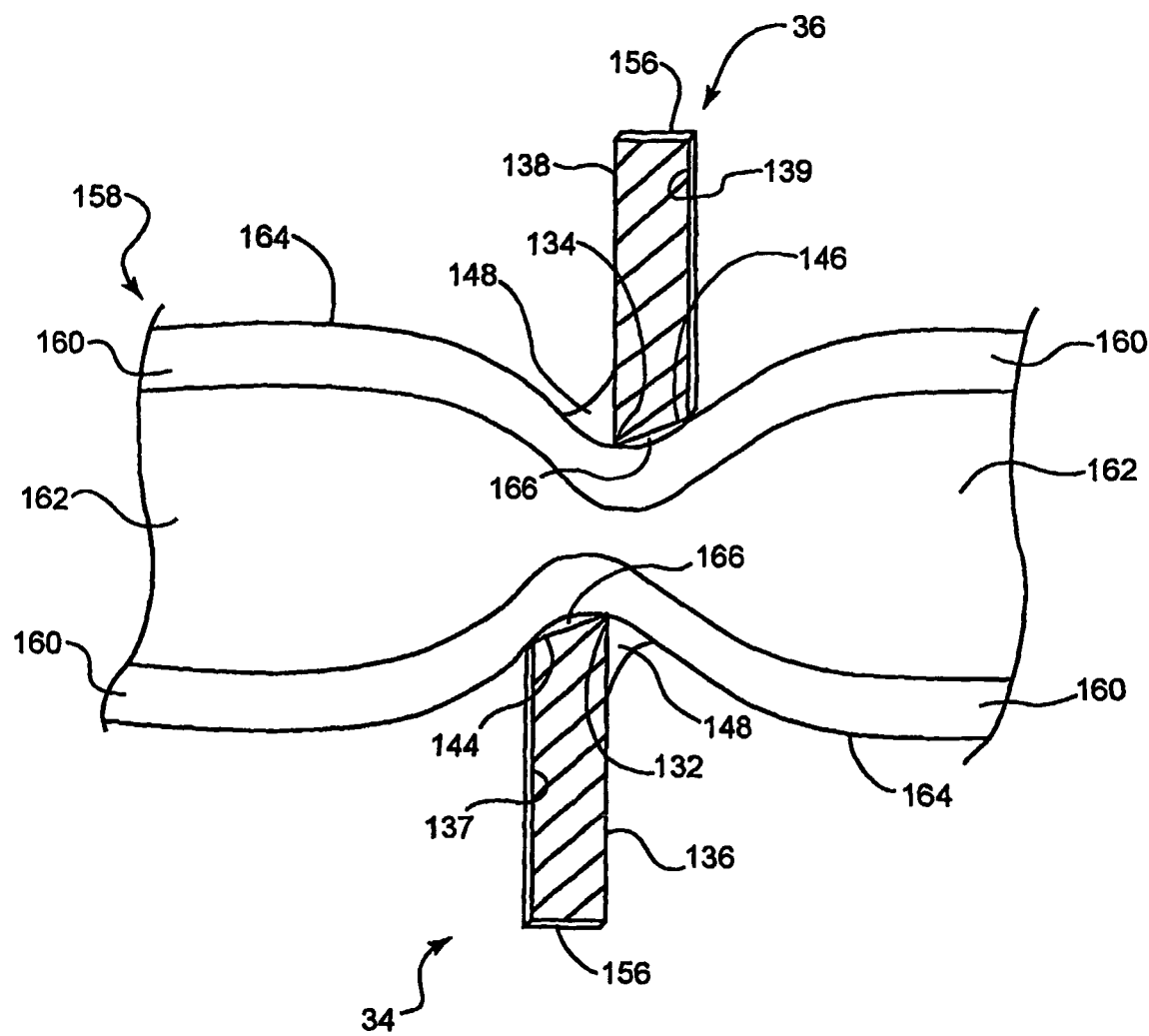
FIG. 11 is a schematic, close-up, cross-sectional view taken along line 11-11 of FIG. 10 with tissue located between the blade members.

While exterior bulbous portion 154 is configured to coagulate tissue, blade members 34, 36 are also used to coagulate and cut tissue, and particularly seal vessels 158, such as blood vessels, as shown in FIG. 11. When blade members 34, 36 are electrified and provide RF power to tissue including a blood vessel 158, the collagen in the tissue and forming the wall 160 begins to shrink as discussed above. As the vessel 158 continues to shrink, the lumen 162 goes from being partially occluded to being completely occluded.

Due to tissue irregularities, the surface 164 of the vessel 158 to be treated may be uneven or undulated with microscopic peaks and valleys. Consequently, with conventional scissors, the area of direct electrical coupling of the vessel 158 to the scissors can be limited to the isolated peaks in the tissue surface 164. In this situation, upon the application of RF power to vessel 158, the electrical coupling of only the tissue peaks to the scissors may result in corresponding increase in current density through the electrically coupled peaks which has the ability to desiccate and char the vessel 158 at these isolated locations. In other locations, the electric current in the form of a spark may jump a gap created between a valley in the surface 164 of the vessel 158 and the scissors and burn, or even perforate, the vessel 158.

Also with conventional scissors, there may be a decrease in the electrical coupling between the surface 164 of vessel 158 and scissor surfaces upon tissue shrinkage and/or desiccation during treatment. As tissue shrinks and/or desiccates during treatment, the surface 164 of vessel 158 may loose contact with the scissors, which, similar to above, decreases the area of electrical coupling therebetween and correspondingly increases the current density and associated heat at the locations which remain electrically coupled. This difficulty is further exacerbated if the tissue is undulated as described above.

To offset a decrease in electrical coupling between the scissors and vessel 158 as the vessel shrinks, the user of conventional scissors may be required to further close or push the scissors into increased contact with the vessel 158. However, with the increased force placed on the vessel 158, there may be increased risk of inadvertently severing the vessel with a shearing edges 132, 134 of the scissors before the vessel is completely occluded.

As shown in FIG. 11, in addition to direct electrical coupling of the surface 164 of vessel 158 to the tissue abutting surfaces 144, 146 of blade members 34, 36, the surface 164 of vessel 158 is indirectly coupled to the shearing surfaces 136, 138 of blade members through fluid coupling 148 comprising an electrically conductive fluid 84. Furthermore, fluid coupling 148 couples the tissue abutting surfaces 144, 146 of blade members 34, 36 at locations where there may be a gap 166 and no direct contact between the surface 164 of vessel 158 to the tissue abutting surfaces 144, 146 of blade members 34, 36.

The fluid coupling 148, preferably comprising saline, inhibits the desiccation, tissue sticking to the shearing surfaces 136, 138 and tissue abutting surfaces 144, 146 of blade members 34, 36, tissue perforation, char formation, smoke generation and sparking encountered with conventional scissors. When an electrically conductive fluid 84 such as saline is used, the fluid cools the tissue while at the same time better dispersing the electrical current into the tissue more uniformly to inhibit heating of the tissue to where desiccation, charring, smoking, sticking and burning occur.

In addition to fluid coupling 148 offsetting (reducing) increases in current densities associated with undulated tissue, or tissue otherwise poorly coupled to the device, fluid coupling 148 also offsets increases in current densities due to so called "edge effects" often associated with sharp edges of electrodes. For example, the sharpness of shearing edges 132, 134 of device 22 may give rise to an increase in current density into tissue adjacent thereto. In providing fluid coupling 148 adjacent each side of shearing edges 132, 134, the increase in current density will be offset by the presence of fluid coupling 148 which spreads the electrical current transmission into the tissue over a larger surface area.

Figure 12:
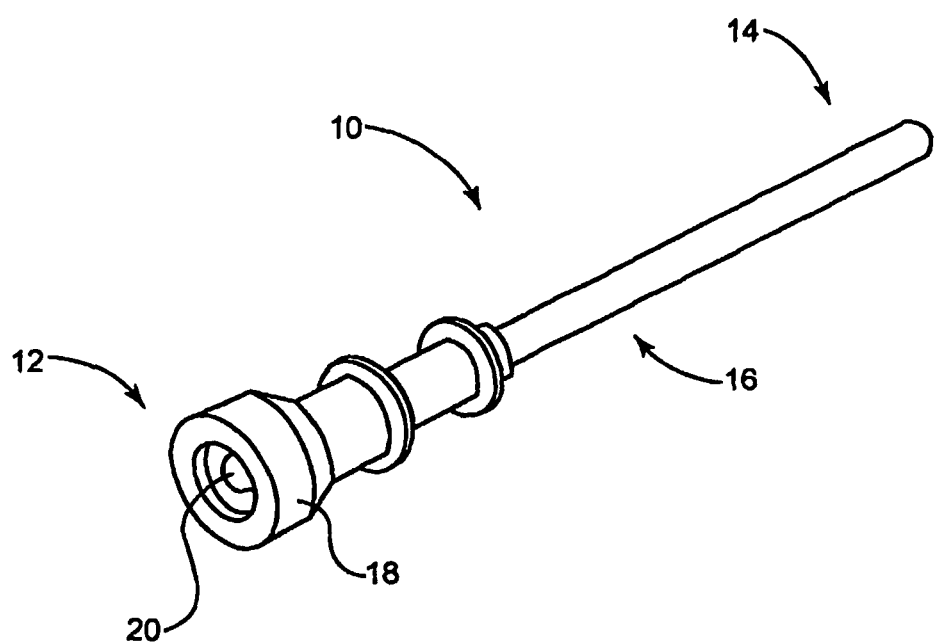
FIG. 12 is an isometric view of a cannula which may be used with the device of the present invention.

As previously disclosed, the electrosurgical devices 22 disclosed herein may be used in conjunction with a cannula as illustrated in FIG. 12 at reference character 10, during laparoscopic surgery such as, for example, a laparoscopic cholecystectomy. Cannula 10 comprises a proximal portion 12 separated from a distal portion 14 by an elongated rigid shaft portion 16. Proximal portion 12 of cannula 10 preferably comprises a head portion 18 connected to rigid shaft portion 16, preferably by threaded engagement. Most importantly, cannula 10 has a working channel 20 which extends through head portion 18 and shaft portion 16 from proximal portion 12 to distal portion 14 of cannula 10. In one particular embodiment, during insertion into cannula 10, the electrosurgical devices disclosed herein configured to enter the proximal end of working channel 20, move along the channel 20 distally, and then be extended from the distal end of the working channel 20. In the same embodiment, during retraction from cannula 10, electrosurgical devices disclosed herein are configured to enter the distal end of working channel 20, move along the channel 20 proximally, and then be removed from the proximal end of working channel 20.

For purposes of the appended claims, the term "tissue" includes, but is not limited to, organs (e.g. liver, lung, spleen, gallbladder), highly vascular tissues (e.g. liver, spleen), soft tissues, hard tissues and tissue masses (e.g. tumors).

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

For example, while the above description of the coupling and operation between rod 54 and first and second handle members 46, 48 has been presented in detail, it should be understood not to constitute a limitation of the invention and that a variety of mechanisms may be employed. Similarly to the coupling and operation between rod 54 and first and second handle members 46, 48, the coupling of blade members 34, 36 to the distal end portion 58 of rod 54 for controlling or effecting the relative movement of blade members 34, 36 at the distal end of device 22 may be performed by a variety of mechanisms known in the art and the specific structures disclosed should be understood not to constitute a limitation of the invention.

Furthermore, it should be understood that the appended claims do not necessarily comprise the broadest scope of the invention which the Applicant is entitled to claim, or the only manner(s) in which the invention may be claimed, or that all recited features are necessary.

We claim:

1. A fluid-assisted electrosurgical scissors to treat tissue, the scissors comprising:

an end effector comprising a first blade member and a second blade member, the first blade member and the second blade member pivotally connected and arranged to cut tissue;

at least one of the first blade member and the second blade member electrically coupled to an electrical connector connectable to a radio frequency power source;

the first blade member comprising a first blade member shearing edge extending to a distal end of the first blade member and the second blade member comprising a second blade member shearing edge extending to a distal end of the second blade member;

the first blade member comprising a first blade member distal portion and the second blade member comprising a second blade member distal portion, wherein at least one of the distal portions further comprises a bulbous portion protruding from a respective one of the first blade member or second blade member, the bulbous portion being bulbous relative to a remainder of the respective one of the first blade member or the second blade member, wherein the bulbous portion has an exposed electrically-conductive surface;

a fluid passage in fluid communication with at least one fluid outlet, wherein the at least one fluid outlet is positioned to expel fluid to the end effector;

a shaft having a first lumen, wherein the end effector is connected to the shaft; and a rod having a second lumen providing a portion of the fluid passage, wherein a portion of the rod is positioned in the first lumen.

2. The electrosurgical scissors of claim 1, wherein the rod comprises a first end positioned in the first lumen and a second end connected to a fluid line.

3. The electrosurgical scissors of claim 1, wherein the at least one fluid outlet is located within the shaft.

4. The electrosurgical scissors of claim 1, wherein:

the first blade member comprises a first blade member exterior surface;

the second blade member comprises a second blade member exterior surface;

at least one of the exterior surfaces is configured to slide along tissue at the treatment site such that fluid expelled from the at least one fluid outlet creates a fluid coupling between the exterior surface and the tissue; and radio frequency power is provided to the tissue from the scissors.

5. A fluid-assisted electrosurgical scissors to treat tissue, the scissors comprising:

an end effector comprising a first blade member and a second blade member, the first blade member and the second blade member pivotally connected and arranged to cut tissue;

at least one of the first blade member and the second blade member electrically coupled to an electrical connector connectable to a radio frequency power source;

the first blade member comprising a first blade member shearing edge extending to a distal end of the first blade member and the second blade member comprising a second blade member shearing edge extending to a distal end of the second blade member;

the first blade member comprising a first blade member distal portion and the second blade member comprising a second blade member distal portion, wherein at least one of the distal portions further comprises a bulbous portion protruding from an exterior side of a respective one of the first blade member or second blade member, the bulbous portion being bulbous relative to a remainder of the respective one of the first blade member or second blade member, wherein:

the bulbous portion has an exposed electrically-conductive surface serving as an electrode pole configured to operate in a monopolar configuration, the exposed electrically-conductive surface facing opposite of an interior side surface of the respective blade member which is provided with the shearing edge;

a fluid passage in fluid communication with at least one fluid outlet; and the at least one fluid outlet positioned to expel a fluid to the end effector to create a fluid coupling between the end effector and tissue at a treatment site and wherein the at least one fluid outlet is obstructed from contact with tissue by at least one of the blade members.

6. The electrosurgical scissors of claim 5 are monopolar electrosurgical scissors.

7. The electrosurgical scissors of claim 5 are laparoscopic electrosurgical scissors.

8. The electrosurgical scissors of claim 5 wherein:
the first blade member comprises a first blade member exterior surface;
the second blade member comprises a second blade member exterior surface; and
at least one of the first blade member exterior surface and the second blade member exterior surface at least partially comprises an electrically insulative material.

9. The electrosurgical scissors of claim 5 wherein:
the first blade member comprises a first blade member shearing surface;
the second blade member comprises a second blade member shearing surface; and
the first blade member shearing surface and the second blade member shearing surface face one another when the first blade member and the second blade member are in a closed position.

10. The electrosurgical scissors of claim 5 further comprising:
a push rod;
a lumen located within the push rod; and
the lumen providing a portion of the fluid passage.

11. The electrosurgical scissors of claim 5 wherein:
the fluid passage passes through a connector member which couples the blade members to a push rod.

12. The electrosurgical scissors of claim 5 wherein:
the at least one fluid outlet is provided by a connector member which couples the blade members and a push rod.

13. The electrosurgical scissors of claim 5 wherein:
at least one of the blade members is curved.

14. The electrosurgical scissors of claim 5 wherein:
the first blade member comprises a first blade member exterior surface;
the second blade member comprises a second blade member exterior surface;
at least one of the exterior surfaces is configured to slide along the tissue at the treatment site such that the fluid coupling is between the exterior surface and the tissue; and
radio frequency power is provided to the tissue from the scissors.

15. The electrosurgical scissors of claim 5 wherein:
the first blade member distal portion and the second blade member distal portion each comprise a bulbous portion protruding from the exterior side of each respective blade member.

16. The electrosurgical scissors of claim 5 wherein:
the bulbous portion protrudes from a convex side of the respective blade member.

17. The electrosurgical Scissors of claim 5 wherein:
the bulbous portion is hemispherical.

18. The electrosurgical scissors of claim 17 wherein:
the exposed electrically-conductive surface of the hemispherical bulbous portion is a hemispherical surface.

19. The electrosurgical scissors of claim 5 wherein:
the at least one fluid outlet is further positioned to provide fluid adjacent each side of at least one of the shearing edges.

20. The electrosurgical scissors of claim 5 wherein:
the bulbous portion is located only on the exterior side of the respective blade member.

* * * * *